US012245930B2

United States Patent
Bor

(10) Patent No.: US 12,245,930 B2
(45) Date of Patent: Mar. 11, 2025

(54) SYSTEM AND METHODS FOR COMPENSATING FOR INTRAOCULAR LENS TILT

(71) Applicant: Alcon Inc., Fribourg (CH)

(72) Inventor: Zsolt Bor, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/740,977

(22) Filed: Jun. 12, 2024

(65) Prior Publication Data

US 2025/0000642 A1    Jan. 2, 2025

Related U.S. Application Data

(60) Provisional application No. 63/511,306, filed on Jun. 30, 2023.

(51) Int. Cl.
*A61F 2/16* (2006.01)
*A61F 9/008* (2006.01)

(52) U.S. Cl.
CPC ............... *A61F 2/16* (2013.01); *A61F 9/008* (2013.01); *A61F 2002/1683* (2013.01); *A61F 2009/00851* (2013.01); *A61F 2250/0006* (2013.01)

(58) Field of Classification Search
CPC .... A61F 2/16; A61F 9/008; A61F 2002/1683; A61F 2009/00851; A61F 2250/0006
USPC .......................................................... 606/4
See application file for complete search history.

(56) References Cited

U.S. PATENT DOCUMENTS

| | | | |
|---|---|---|---|
| 3,915,172 A | 10/1975 | Wichterle et al. |
| 4,253,199 A | 3/1981 | Banko |
| 4,273,109 A | 6/1981 | Enderby |
| 4,298,996 A | 11/1981 | Barnet |
| 4,304,895 A | 12/1981 | Loshaek |
| 4,373,218 A | 2/1983 | Schachar |
| 4,423,809 A | 1/1984 | Mazzocco |
| 4,435,855 A | 3/1984 | Pannu |

(Continued)

FOREIGN PATENT DOCUMENTS

| | | |
|---|---|---|
| CN | 1283974 | 2/2001 |
| CN | 1367667 | 9/2002 |

(Continued)

OTHER PUBLICATIONS

Baughman et al. "Negative poisson's ratios for extreme states of matter," *Science*, vol. 288, pp. 2018-2022, Jun. 16, 2000.

(Continued)

*Primary Examiner* — Aaron F Roane
(74) *Attorney, Agent, or Firm* — Levine Bagade Han LLP

(57) ABSTRACT

Disclosed herein are systems and methods for compensating for a tilt of an intraocular lens (IOL) and systems and methods for adjusting the IOL. For example, one of the methods can comprise capturing one or more optical coherence tomography (OCT) images of an eye of a subject when the IOL is implanted within the eye of the subject. The method can also comprise generating a fixation target such that the fixation target is visible to the eye of the subject and moving the fixation target until a transverse plane of the IOL is perpendicular or substantially perpendicular to an optical axis of an ophthalmic system. The method can also comprise directing a laser beam generated by a laser of the ophthalmic system at the IOL.

20 Claims, 9 Drawing Sheets

(56) References Cited

U.S. PATENT DOCUMENTS

| | | |
|---|---|---|
| 4,461,294 A | 7/1984 | Baron |
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,538,608 A | 9/1985 | L'Esperance |
| 4,558,698 A | 12/1985 | O'Dell |
| 4,566,438 A | 1/1986 | Liese et al. |
| 4,604,087 A | 8/1986 | Joseph |
| 4,617,715 A | 10/1986 | Koistinen et al. |
| 4,633,866 A | 1/1987 | Peyman et al. |
| 4,634,418 A | 1/1987 | Binder |
| 4,685,921 A | 8/1987 | Peyman |
| 4,685,922 A | 8/1987 | Peyman |
| 4,693,717 A | 9/1987 | Michelson |
| 4,722,724 A | 2/1988 | Schocket |
| 4,729,373 A | 3/1988 | Peyman |
| 4,731,079 A | 3/1988 | Stoy |
| 4,750,901 A | 6/1988 | Molteno |
| 4,770,654 A | 9/1988 | Rogers et al. |
| 4,781,719 A | 11/1988 | Kelman |
| 4,784,485 A | 11/1988 | Ho |
| 4,819,631 A | 4/1989 | Poley |
| 4,842,601 A | 6/1989 | Smith |
| 4,848,343 A | 7/1989 | Wallsten et al. |
| 4,861,341 A | 8/1989 | Woodburn |
| 4,863,457 A | 9/1989 | Lee |
| 4,876,250 A | 10/1989 | Clark |
| 4,880,000 A | 11/1989 | Holmes et al. |
| 4,902,293 A | 2/1990 | Feaster |
| 4,906,247 A | 3/1990 | Fritch |
| 4,911,714 A | 3/1990 | Poley |
| 4,934,363 A | 6/1990 | Smith et al. |
| 4,934,809 A | 6/1990 | Volk |
| 4,946,436 A | 8/1990 | Smith |
| 4,963,148 A | 10/1990 | Sulc et al. |
| 4,994,060 A | 2/1991 | Rink et al. |
| 4,995,880 A | 2/1991 | Galib |
| 5,035,710 A | 7/1991 | Nakada et al. |
| 5,047,051 A | 9/1991 | Cumming |
| 5,066,301 A | 11/1991 | Wiley |
| 5,100,410 A | 3/1992 | Dulebohn |
| 5,108,429 A | 4/1992 | Wiley |
| 5,123,902 A | 6/1992 | Muller et al. |
| 5,127,901 A | 7/1992 | Odrich |
| 5,145,935 A | 9/1992 | Hayashi |
| 5,152,789 A | 10/1992 | Willis |
| 5,171,241 A | 12/1992 | Buboltz et al. |
| 5,171,266 A | 12/1992 | Wiley et al. |
| 5,180,362 A | 1/1993 | Worst |
| 5,235,003 A | 8/1993 | Ward et al. |
| 5,238,004 A | 8/1993 | Sahatjian et al. |
| 5,251,993 A | 10/1993 | Sigourney |
| 5,254,112 A | 10/1993 | Sinofsky et al. |
| 5,275,624 A | 1/1994 | Hara et al. |
| 5,304,182 A | 4/1994 | Rheinish et al. |
| 5,326,347 A | 7/1994 | Cumming |
| 5,342,370 A | 8/1994 | Simon et al. |
| 5,354,333 A | 10/1994 | Kammann et al. |
| 5,360,399 A | 11/1994 | Stegmann |
| 5,371,078 A | 12/1994 | Clark et al. |
| 5,372,577 A | 12/1994 | Ungerleider |
| 5,391,590 A | 2/1995 | Gerace et al. |
| 5,423,777 A | 6/1995 | Tajiri et al. |
| 5,426,166 A | 6/1995 | Usifer et al. |
| 5,444,135 A | 8/1995 | Cheradame et al. |
| 5,445,637 A | 8/1995 | Bretton |
| 5,454,796 A | 10/1995 | Krupin |
| 5,468,246 A | 11/1995 | Blake |
| 5,489,302 A | 2/1996 | Skottun |
| 5,549,614 A | 8/1996 | Tunis |
| 5,562,676 A | 10/1996 | Brady et al. |
| 5,578,081 A | 11/1996 | Mcdonald |
| 5,585,049 A | 12/1996 | Grisoni et al. |
| 5,591,223 A | 1/1997 | Lock et al. |
| 5,593,436 A | 1/1997 | Langerman |
| 5,628,795 A | 5/1997 | Langerman |
| 5,633,504 A | 5/1997 | Collins et al. |
| 5,651,782 A | 7/1997 | Simon et al. |
| 5,653,753 A | 8/1997 | Brady et al. |
| 5,676,669 A | 10/1997 | Colvard |
| 5,676,944 A | 10/1997 | Alvarado et al. |
| 5,684,637 A | 11/1997 | Floyd |
| 5,713,844 A | 2/1998 | Peyman |
| 5,735,858 A | 4/1998 | Makker et al. |
| 5,738,677 A | 4/1998 | Colvard et al. |
| 5,767,669 A | 6/1998 | Hansen et al. |
| 5,776,138 A | 7/1998 | Vidal et al. |
| 5,803,925 A | 9/1998 | Yang et al. |
| 5,807,302 A | 9/1998 | Wandel |
| 5,868,697 A | 2/1999 | Richter et al. |
| 5,868,751 A | 2/1999 | Feingold |
| 5,873,879 A | 2/1999 | Figueroa et al. |
| RE36,150 E | 3/1999 | Gupta |
| 5,885,279 A | 3/1999 | Bretton |
| 5,919,171 A | 7/1999 | Kira et al. |
| 5,993,438 A | 11/1999 | Juhasz et al. |
| 6,001,107 A | 12/1999 | Feingold |
| 6,002,480 A | 12/1999 | Izatt et al. |
| 6,048,348 A | 4/2000 | Chambers et al. |
| 6,050,999 A | 4/2000 | Paraschac et al. |
| 6,102,045 A | 8/2000 | Nordquist et al. |
| 6,146,375 A | 11/2000 | Juhasz et al. |
| 6,152,918 A | 11/2000 | Padilla et al. |
| 6,188,526 B1 | 2/2001 | Sasaya et al. |
| 6,225,367 B1 | 5/2001 | Chaouk et al. |
| 6,229,641 B1 | 5/2001 | Kosaka |
| 6,238,409 B1 | 5/2001 | Hojeibane |
| 6,251,090 B1 | 6/2001 | Avery et al. |
| 6,283,975 B1 | 9/2001 | Glick et al. |
| 6,283,976 B1 | 9/2001 | Portney |
| 6,336,932 B1 | 1/2002 | Figueroa et al. |
| 6,342,073 B1 | 1/2002 | Cumming et al. |
| 6,387,101 B1 | 5/2002 | Butts et al. |
| 6,398,789 B1 | 6/2002 | Capetan |
| 6,406,481 B2 | 6/2002 | Feingold et al. |
| 6,406,494 B1 | 6/2002 | Laguette et al. |
| 6,436,092 B1 | 8/2002 | Peyman |
| 6,464,724 B1 | 10/2002 | Lynch et al. |
| 6,464,725 B2 | 10/2002 | Skotton |
| 6,488,708 B2 | 12/2002 | Sarfarazi |
| 6,491,697 B1 | 12/2002 | Clark et al. |
| 6,497,708 B1 | 12/2002 | Cumming |
| 6,503,275 B1 | 1/2003 | Cumming |
| 6,508,779 B1 | 1/2003 | Suson |
| 6,508,803 B1 | 1/2003 | Horikawa et al. |
| 6,510,600 B2 | 1/2003 | Yaron et al. |
| 6,517,577 B1 | 2/2003 | Callahan et al. |
| 6,533,768 B1 | 3/2003 | Hill |
| 6,537,283 B2 | 3/2003 | Van Noy |
| 6,552,860 B1 | 4/2003 | Alden |
| 6,585,768 B2 | 7/2003 | Hamano et al. |
| 6,599,317 B1 | 7/2003 | Weinschenk et al. |
| 6,601,956 B1 | 8/2003 | Jean et al. |
| 6,605,093 B1 | 8/2003 | Blake |
| 6,610,350 B2 | 8/2003 | Suzuki et al. |
| 6,616,691 B1 | 9/2003 | Tran |
| 6,616,692 B1 | 9/2003 | Glick et al. |
| 6,626,858 B2 | 9/2003 | Lynch et al. |
| 6,638,239 B1 | 10/2003 | Bergheim et al. |
| 6,638,306 B2 | 10/2003 | Cumming |
| 6,645,245 B1 | 11/2003 | Preussner |
| 6,660,035 B1 | 12/2003 | Lang et al. |
| 6,676,607 B2 | 1/2004 | De Juan et al. |
| 6,699,210 B2 | 3/2004 | Williams et al. |
| 6,699,211 B2 | 3/2004 | Savage |
| 6,709,108 B2 | 3/2004 | Levine et al. |
| 6,712,848 B1 | 3/2004 | Wolf et al. |
| 6,730,056 B1 | 5/2004 | Ghaem et al. |
| 6,730,123 B1 | 5/2004 | Klopotek |
| 6,783,544 B2 | 8/2004 | Lynch et al. |
| 6,818,158 B2 | 11/2004 | Pham et al. |
| 6,827,699 B2 | 12/2004 | Lynch et al. |

(56) References Cited

U.S. PATENT DOCUMENTS

| | | |
|---|---|---|
| 6,827,738 B2 | 12/2004 | Willis et al. |
| 6,881,198 B2 | 4/2005 | Brown |
| 6,923,815 B2 | 8/2005 | Brady et al. |
| 6,926,736 B2 | 8/2005 | Peng et al. |
| 6,949,093 B1 | 9/2005 | Peyman |
| 7,001,374 B2 | 2/2006 | Peyman |
| 7,060,094 B2 | 6/2006 | Shahinpoor et al. |
| 7,147,650 B2 | 12/2006 | Lee |
| 7,163,543 B2 | 1/2007 | Smedley et al. |
| 7,186,232 B1 | 3/2007 | Smedley et al. |
| 7,207,980 B2 | 4/2007 | Christian et al. |
| 7,297,130 B2 | 11/2007 | Bergheim et al. |
| 7,311,194 B2 | 12/2007 | Jin et al. |
| 7,331,984 B2 | 2/2008 | Tu et al. |
| 7,438,723 B2 | 10/2008 | Esch |
| 7,615,073 B2 | 11/2009 | Deacon et al. |
| 7,637,947 B2 | 12/2009 | Smith et al. |
| 7,753,953 B1 | 7/2010 | Yee |
| 7,759,408 B2 | 7/2010 | Schorzman et al. |
| 7,988,290 B2 | 8/2011 | Campbell et al. |
| 8,012,115 B2 | 9/2011 | Karageozian |
| 8,052,752 B2 | 11/2011 | Woods et al. |
| 8,308,701 B2 | 11/2012 | Horvath et al. |
| 8,475,526 B2 | 7/2013 | Pynson |
| 8,480,734 B2 | 7/2013 | Kellan et al. |
| 8,613,766 B2 | 12/2013 | Richardson et al. |
| 8,641,748 B2 | 2/2014 | Hebert et al. |
| 8,961,447 B2 | 2/2015 | Schieber et al. |
| 8,968,328 B2 | 3/2015 | Ichinohe et al. |
| 8,968,396 B2 | 3/2015 | Matthews et al. |
| 9,066,783 B2 | 6/2015 | Euteneuer et al. |
| 9,277,987 B2 | 3/2016 | Smiley et al. |
| 9,351,874 B2 | 5/2016 | Schieber et al. |
| 9,358,156 B2 | 6/2016 | Wardle et al. |
| 9,693,901 B2 | 7/2017 | Horvath et al. |
| 9,795,503 B2 | 10/2017 | Perez et al. |
| 10,195,020 B2 | 2/2019 | Matthews |
| 10,299,913 B2 | 5/2019 | Smiley et al. |
| 10,357,356 B2 | 7/2019 | Smiley et al. |
| 10,433,949 B2 | 10/2019 | Smiley et al. |
| 10,617,558 B2 | 4/2020 | Schieber et al. |
| 11,426,270 B2 | 8/2022 | Hildebrand et al. |
| 11,660,182 B2 | 5/2023 | Smiley et al. |
| 2002/0003546 A1 | 1/2002 | Mochimaru et al. |
| 2002/0013553 A1 | 1/2002 | Pajunk et al. |
| 2002/0055776 A1 | 5/2002 | Juan et al. |
| 2002/0072673 A1 | 6/2002 | Yamamoto et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0161434 A1 | 10/2002 | Laguette et al. |
| 2002/0169130 A1 | 11/2002 | Tu et al. |
| 2002/0193804 A1 | 12/2002 | Tickle |
| 2002/0193876 A1 | 12/2002 | Lang et al. |
| 2003/0014092 A1 | 1/2003 | Neuhann |
| 2003/0018384 A1 | 1/2003 | Valyunin et al. |
| 2003/0040754 A1 | 2/2003 | Mitchell et al. |
| 2003/0060878 A1 | 3/2003 | Shadduck |
| 2003/0069637 A1 | 4/2003 | Lynch et al. |
| 2003/0078657 A1 | 4/2003 | Zadno-Azizi et al. |
| 2003/0109926 A1 | 6/2003 | Portney |
| 2003/0120200 A1 | 6/2003 | Bergheim |
| 2003/0125351 A1 | 7/2003 | Azuma et al. |
| 2003/0135272 A1 | 7/2003 | Brady et al. |
| 2003/0149480 A1 | 8/2003 | Shadduck |
| 2003/0180522 A1 | 9/2003 | DeSimone et al. |
| 2003/0181848 A1 | 9/2003 | Bergheim et al. |
| 2003/0183960 A1 | 10/2003 | Buazza et al. |
| 2003/0187384 A1 | 10/2003 | Bergheim |
| 2003/0199977 A1 | 10/2003 | Cumming |
| 2003/0229303 A1 | 12/2003 | Haffner et al. |
| 2004/0001180 A1 | 1/2004 | Epstein |
| 2004/0015236 A1 | 1/2004 | Sarfarazi |
| 2004/0024345 A1 | 2/2004 | Gharib et al. |
| 2004/0024453 A1 | 2/2004 | Castillejos |
| 2004/0059343 A1 | 3/2004 | Shearer et al. |
| 2004/0066489 A1 | 4/2004 | Benedikt et al. |
| 2004/0073156 A1 | 4/2004 | Brown |
| 2004/0082939 A1 | 4/2004 | Berlin |
| 2004/0082994 A1 | 4/2004 | Woods et al. |
| 2004/0088048 A1 | 5/2004 | Richter et al. |
| 2004/0088050 A1 | 5/2004 | Norrby et al. |
| 2004/0092856 A1 | 5/2004 | Dahan |
| 2004/0098124 A1 | 5/2004 | Freeman et al. |
| 2004/0106975 A1 | 6/2004 | Solovay et al. |
| 2004/0111152 A1 | 6/2004 | Kelman |
| 2004/0122380 A1 | 6/2004 | Utterberg |
| 2004/0127843 A1 | 7/2004 | Tu et al. |
| 2004/0127984 A1 | 7/2004 | Paul et al. |
| 2004/0147870 A1 | 7/2004 | Burns et al. |
| 2004/0181279 A1 | 9/2004 | Nun |
| 2004/0210185 A1 | 10/2004 | Tu et al. |
| 2004/0225357 A1 | 11/2004 | Worst et al. |
| 2004/0230203 A1 | 11/2004 | Yaguchi |
| 2004/0249333 A1 | 12/2004 | Bergheim |
| 2004/0254520 A1 | 12/2004 | Porteous et al. |
| 2005/0041200 A1 | 2/2005 | Rich |
| 2005/0049578 A1 | 3/2005 | Tu et al. |
| 2005/0060016 A1 | 3/2005 | Wu et al. |
| 2005/0107734 A1 | 5/2005 | Coroneo |
| 2005/0113911 A1 | 5/2005 | Peyman |
| 2005/0146685 A1 | 7/2005 | Hanaki et al. |
| 2005/0149080 A1 | 7/2005 | Hunter et al. |
| 2005/0149183 A1 | 7/2005 | Shadduck |
| 2005/0171507 A1 | 8/2005 | Christian et al. |
| 2005/0182350 A1 | 8/2005 | Nigam |
| 2005/0191331 A1 | 9/2005 | Hunter et al. |
| 2005/0197613 A1 | 9/2005 | Sniegowski et al. |
| 2005/0209549 A1 | 9/2005 | Bergheim |
| 2005/0209555 A1 | 9/2005 | Middleton et al. |
| 2005/0222577 A1 | 10/2005 | Vaquero |
| 2005/0222579 A1 | 10/2005 | Vaquero et al. |
| 2005/0251253 A1 | 11/2005 | Gross |
| 2005/0251254 A1 | 11/2005 | Brady et al. |
| 2005/0255231 A1 | 11/2005 | Hill et al. |
| 2006/0021623 A1 | 2/2006 | Miller et al. |
| 2006/0084907 A1 | 4/2006 | Bergheim |
| 2006/0100701 A1 | 5/2006 | Esch et al. |
| 2006/0116626 A1 | 6/2006 | Smedley et al. |
| 2006/0135642 A1 | 6/2006 | Makker et al. |
| 2006/0155265 A1 | 7/2006 | Juhasz et al. |
| 2006/0178674 A1 | 8/2006 | Mcintyre |
| 2006/0195187 A1 | 8/2006 | Stegmann et al. |
| 2006/0246112 A1 | 11/2006 | Snyder et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0027538 A1 | 2/2007 | Aharoni et al. |
| 2007/0093794 A1 | 4/2007 | Wang et al. |
| 2007/0100444 A1 | 5/2007 | Brady et al. |
| 2007/0106200 A1 | 5/2007 | Levy |
| 2007/0129717 A1 | 6/2007 | Brown et al. |
| 2007/0156236 A1 | 7/2007 | Stenger |
| 2007/0162112 A1 | 7/2007 | Burriesci et al. |
| 2007/0191863 A1 | 8/2007 | De Juan et al. |
| 2007/0203578 A1 | 8/2007 | Scholl et al. |
| 2007/0213817 A1 | 9/2007 | Esch et al. |
| 2007/0219509 A1 | 9/2007 | Tashiro et al. |
| 2007/0244561 A1 | 10/2007 | Ben Nun |
| 2007/0260157 A1 | 11/2007 | Norrby |
| 2007/0260308 A1 | 11/2007 | Tran |
| 2007/0276315 A1 | 11/2007 | Haffner et al. |
| 2007/0282245 A1 | 12/2007 | Tu et al. |
| 2007/0282438 A1 | 12/2007 | Hong et al. |
| 2007/0293872 A1 | 12/2007 | Peyman |
| 2007/0298068 A1 | 12/2007 | Badawi et al. |
| 2007/0299487 A1 | 12/2007 | Shadduck |
| 2008/0004699 A1 | 1/2008 | Ben Nun |
| 2008/0015488 A1 | 1/2008 | Tu et al. |
| 2008/0027537 A1 | 1/2008 | Gerlach et al. |
| 2008/0045878 A1 | 2/2008 | Bergheim |
| 2008/0065096 A1 | 3/2008 | Kappelhof et al. |
| 2008/0082088 A1 | 4/2008 | Kurtz et al. |
| 2008/0119827 A1 | 5/2008 | Kurtz et al. |

(56) References Cited

U.S. PATENT DOCUMENTS

| | | |
|---|---|---|
| 2008/0119865 A1 | 5/2008 | Meunier et al. |
| 2008/0139769 A1 | 6/2008 | Iwamoto et al. |
| 2008/0195027 A1 | 8/2008 | Coroneo |
| 2008/0200860 A1 | 8/2008 | Tu et al. |
| 2008/0200982 A1 | 8/2008 | Your |
| 2008/0234624 A2 | 9/2008 | Bergheim et al. |
| 2008/0269887 A1 | 10/2008 | Cumming |
| 2008/0269987 A1 | 10/2008 | Barron et al. |
| 2008/0300680 A1 | 12/2008 | Joshua |
| 2008/0306587 A1 | 12/2008 | Your |
| 2008/0312661 A1 | 12/2008 | Downer et al. |
| 2009/0005852 A1 | 1/2009 | Gittings et al. |
| 2009/0005865 A1 | 1/2009 | Smiley et al. |
| 2009/0018512 A1 | 1/2009 | Charles |
| 2009/0030415 A1 | 1/2009 | Gogolewski |
| 2009/0030425 A1 | 1/2009 | Smiley et al. |
| 2009/0036819 A1 | 2/2009 | Tu et al. |
| 2009/0036840 A1 | 2/2009 | Viray et al. |
| 2009/0036898 A1 | 2/2009 | Ichinohe et al. |
| 2009/0043321 A1 | 2/2009 | Conston et al. |
| 2009/0069786 A1 | 3/2009 | Vesely et al. |
| 2009/0076602 A1 | 3/2009 | Ho et al. |
| 2009/0079940 A1 | 3/2009 | Dai et al. |
| 2009/0082860 A1 | 3/2009 | Schieber et al. |
| 2009/0112313 A1 | 4/2009 | Mentak |
| 2009/0118718 A1 | 5/2009 | Raksi et al. |
| 2009/0124773 A1 | 5/2009 | Zhou et al. |
| 2009/0155371 A1 | 6/2009 | Sojka et al. |
| 2009/0171366 A1 | 7/2009 | Tanaka |
| 2009/0204053 A1 | 8/2009 | Nissan et al. |
| 2009/0204123 A1 | 8/2009 | Downer |
| 2009/0227934 A1 | 9/2009 | Euteneuer et al. |
| 2009/0228101 A1 | 9/2009 | Zadno-Azizi |
| 2009/0234449 A1 | 9/2009 | De Juan et al. |
| 2009/0259126 A1 | 10/2009 | Saal et al. |
| 2009/0270876 A1 | 10/2009 | Hoffmann et al. |
| 2009/0281520 A1 | 11/2009 | Highley et al. |
| 2009/0292293 A1 | 11/2009 | Bogaert et al. |
| 2009/0306774 A1 | 12/2009 | Park |
| 2009/0312836 A1 | 12/2009 | Pinchuk et al. |
| 2009/0318933 A1 | 12/2009 | Anderson |
| 2010/0010416 A1 | 1/2010 | Juan et al. |
| 2010/0016965 A1 | 1/2010 | Hong et al. |
| 2010/0063588 A1 | 3/2010 | Park |
| 2010/0069522 A1 | 3/2010 | Linhardt et al. |
| 2010/0094412 A1 | 4/2010 | Wensrich |
| 2010/0130985 A1 | 5/2010 | Tanaka |
| 2010/0137981 A1 | 6/2010 | Silvestrini et al. |
| 2010/0161049 A1 | 6/2010 | Inoue |
| 2010/0173866 A1 | 7/2010 | Hee et al. |
| 2010/0262174 A1 | 10/2010 | Sretavan et al. |
| 2010/0280317 A1 | 11/2010 | Silvestrini et al. |
| 2011/0028883 A1 | 2/2011 | Juan et al. |
| 2011/0028950 A1 | 2/2011 | Raksi et al. |
| 2011/0105990 A1 | 5/2011 | Silvestrini |
| 2011/0118834 A1 | 5/2011 | Lo et al. |
| 2011/0208301 A1 | 8/2011 | Anvar et al. |
| 2011/0288638 A1 | 11/2011 | Smiley et al. |
| 2012/0021397 A1 | 1/2012 | Van Dalen et al. |
| 2012/0035524 A1 | 2/2012 | Silvestrini |
| 2012/0323159 A1 | 12/2012 | Wardle et al. |
| 2013/0103145 A1 | 4/2013 | John et al. |
| 2013/0158462 A1 | 6/2013 | Wardle et al. |
| 2013/0253407 A1 | 9/2013 | Yablonski |
| 2013/0281817 A1 | 10/2013 | Schaller et al. |
| 2014/0031737 A1 | 1/2014 | Silvestrini |
| 2014/0214161 A1 | 7/2014 | Schieber et al. |
| 2014/0309599 A1 | 10/2014 | Schaller |
| 2015/0038893 A1 | 2/2015 | Haffner et al. |
| 2015/0057642 A1 | 2/2015 | Zickler et al. |
| 2015/0126809 A1 | 5/2015 | Silvestrini et al. |
| 2015/0223984 A1 | 8/2015 | Schieber et al. |
| 2015/0238360 A1 | 8/2015 | De Juan et al. |
| 2016/0058552 A1 | 3/2016 | Argal et al. |
| 2017/0049561 A1 | 2/2017 | Smiley et al. |
| 2017/0172800 A1 | 6/2017 | Romoda et al. |
| 2017/0258581 A1 | 9/2017 | Borja et al. |
| 2017/0281334 A1 | 10/2017 | Zhao |
| 2018/0147051 A1 | 5/2018 | Scholl et al. |
| 2018/0153682 A1 | 6/2018 | Hajela et al. |
| 2018/0177589 A1 | 6/2018 | Argento et al. |
| 2018/0200112 A1 | 7/2018 | Krampert et al. |
| 2018/0256315 A1 | 9/2018 | Hildebrand et al. |
| 2019/0053892 A1 | 2/2019 | Siney et al. |
| 2020/0000577 A1 | 1/2020 | Smiley et al. |
| 2020/0246134 A1 | 8/2020 | Hajela et al. |
| 2020/0261266 A1 | 8/2020 | Bley et al. |
| 2020/0315848 A1* | 10/2020 | Rosen ............... A61F 9/00827 |
| 2020/0332085 A1 | 10/2020 | Ebe et al. |
| 2020/0337833 A1 | 10/2020 | Green |
| 2020/0405541 A1 | 12/2020 | Raksi |
| 2021/0100649 A1 | 4/2021 | Smiley |
| 2021/0100650 A1 | 4/2021 | Smiley et al. |
| 2021/0100652 A1 | 4/2021 | Walz et al. |
| 2021/0186320 A1 | 6/2021 | Copland |
| 2023/0191730 A1 | 6/2023 | Walz et al. |
| 2023/0240836 A1 | 8/2023 | Irby et al. |
| 2023/0248509 A1 | 8/2023 | Smiley et al. |
| 2024/0148554 A1 | 5/2024 | Paliwal et al. |

FOREIGN PATENT DOCUMENTS

| | | |
|---|---|---|
| CN | 1378440 | 11/2002 |
| CN | 1384727 | 12/2002 |
| EP | 0898972 | 3/1999 |
| FR | 2655841 | 6/1991 |
| FR | 2784575 | 12/2000 |
| JP | H05(1993)-171056 | 7/1993 |
| JP | 07-044938 | 5/1995 |
| JP | 08-501715 | 2/1996 |
| JP | 08-224295 | 9/1996 |
| JP | 09-294754 | 11/1997 |
| JP | 10-206609 | 8/1998 |
| JP | 11-047168 | 2/1999 |
| JP | 1999-047168 | 2/1999 |
| JP | 11-056998 | 3/1999 |
| JP | 11-169391 | 6/1999 |
| JP | 11-276509 | 10/1999 |
| JP | 11-332903 | 12/1999 |
| JP | 2000-250203 | 9/2000 |
| JP | 2001-502592 | 2/2001 |
| JP | 2003-144387 | 5/2003 |
| JP | 2003-524503 | 8/2003 |
| JP | 2003-530978 | 10/2003 |
| JP | 2006-523130 | 10/2006 |
| JP | 2007-513715 | 5/2007 |
| JP | 2007-516794 | 6/2007 |
| JP | 2007-518447 | 7/2007 |
| JP | 2010-095719 | 4/2010 |
| JP | 2016-138050 | 8/2016 |
| JP | 2017-148614 | 8/2017 |
| SU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2004/081613 | 9/2004 |
| WO | WO 2005/018504 | 3/2005 |
| WO | WO 2005/084588 | 9/2005 |
| WO | WO 2009/015234 | 1/2009 |
| WO | WO 2018/222558 | 12/2018 |
| WO | WO 2018/227014 | 12/2018 |
| WO | WO 2021/067574 | 4/2021 |
| WO | WO 2021/067579 | 4/2021 |
| WO | WO 2022/216451 | 10/2022 |
| WO | WO 2023/122490 | 6/2023 |
| WO | WO 2023/147224 | 8/2023 |

(56) References Cited

FOREIGN PATENT DOCUMENTS

OTHER PUBLICATIONS

Baughman, "Avoiding the shrink," *Nature*, vol. 425, pp. 667, Oct. 16, 2003.
Conlisk, A. T. et al. "Mass Transfer and Flow in Electrically Charged Micro- and Nano-channels," *Analytical Chemistry*, vol. 74; iss. 9; pp. 2139-2150; May 2002.
Dubbelman et al. "The Thickness of the Aging Human Lens Obtained from Corrected Scheimpflug Images," *Optometry & Vision Science*; vo. 78; iss. 6; pp. 411-416; Jun. 2001.
Gorder, P. F.; Electricity can pump medicine in implanted medical devices; Ohio State Research News; 3 pgs.; May 2, 2002 (printed from internet Aug. 19, 2010).
Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.
Gruber et al. "Exhaustive soxhlet extraction for the complete removal of residual compounds," *Journal of Biomedical Materials Research*, vol. 53; No. 5; pp. 445-448; Mar. 2000.
Jeon et al., "Shape memory and nanostructure in poly(norbornyl-POSS) copolymers," *Polymer International*, vol. 49, pp. 453-457, May 2000.
Kim et al., "Polyurethanes having shape memory effects," *Polymer*, vol. 37, No. 26, pp. 5781-5793, Dec. 1996.
Lakes et al., "Dramatically stiffer elastic composite materials due to negative stiffness phase?," *Journal of the Mechanics and Physics of Solids*, vol. 50, pp. 979-1009, May 2002.
Lakes et al., "Extreme damping in composite materials with negative-stiffness inclusions," *Nature*, vol. 410, pp. 565-567, Mar. 29, 2001.
Lakes et al., "Microbuckling instability in elastomeric cellular sollids," *J. Materials Science*, vol. 28, pp. 4667-4672, Janunary 1993.
Lakes, "A broader view of membranes," *Nature*, vol. 414, pp. 503-504, Nov. 29, 2001.
Lakes, "Deformations in extreme matter," *Science*; perspectives; vol. 288; No. 5473; pp. 1976-1977; Jun. 16, 2000.
Lakes, "Extreme damping in compliant composites with a negative-stiffness phase," *Philosophical Magazine Letters*, vol. 81, No. 2, pp. 95-100, Feb. 2001.
Lakes, "Extreme damping in composite materials with a negative stiffness phase," *Physical Review Letters*, vol. 86, No. 13, pp. 2897-2900, Mar. 26, 2001.
Lakes, "Negative poisson's ratio materials," *Science*, vol. 238, pp. 551, Oct. 23, 1987.
Lakes, "No contractile obligations," *Nature*, vol. 358, pp. 713-714, Dec. 31, 1992.
Lendlein et al., "Biodegradable, elastic shape-memory polymers for potential biomedical applications", *Science*; vol. 296; pp. 1673-1676; May 31, 2002.
Lendlein et al., "Shape-memory polymers," *Angew. Chem. Int. Ed.*; vol. 41; pp. 2034-2057; Jun. 2002.
Li et al., "Crystallinity and morphology of segmented polyurethanes with different soft-segment length," *Journal of Applied Polymer Science*, vol. 62, pp. 631-638, Oct. 1996.
Liu et al., "Thermomechanical characterization of a tailored series of shape memory polymers," *Journal of Applied Medical Polymers*, vol. 6, No. 2, Dec. 2002.
Mather et al., "Strain recovery in POSS hybrid thermoplastics," *Polymer Preprints*, vol. 41, No. 1, pp. 528-529, Feb. 2000.
Metcalfe et al., "Cold hibernated elastic memory foams for endovascular interventions," *Biomaterials*, vol. 24, pp. 491-497, Feb. 2003.
Takahashi et al., "Structure and properties of shape-memory polyurethane block copolymers," *Journal of Applied Polymer Science*, vol. 60, pp. 1061-1069, May 1996.
Tehrani et al. "Capsule measuring ring to predict capsular bag diameter and follow its course after foldable intraocular lens implantation," *J Cataract Refract Surg.*; vol. 29; No. 11; pp. 2127-2134; Nov. 29, 2003.
Tobushi et al., "Thermomechanical properties of shape memory polymers of polyurethane series and their applications," *Journal de Physique IV, Colloque C1*, vol. 6, pp. 377-384, Aug. 1996.
Vass et al. "Prediction of pseudophakic capsular bag diameter based on biometric variables," *J Cataract Refract Surg.*; vol. 25; pp. 1376-1381; Oct. 1999.
Wang et al., "Deformation of extreme viscoelastic metals and composites," *Materials Science and Enginerring A*, vol. 370, pp. 41-49, Apr. 15, 2004.
Wang et al., "Extreme stiffness systems due to negative stiffness elements," *American Journal of Physics*, vol. 72, No. 1, pp. 40-50, Jan. 2004.
Wyant et al.; "Basic Wavefront Aberration Theory for Optical Metrology," *Applied Optics and Optical Engineering*, vol. XI, pp. 1, 28-39, Aug. 10, 1992.
Xu et al., "Making negative poisson's ratio microstructures by soft lithography," *Advanced Materials*, vol. 11, No. 14, pp. 1186-1189, Jun. 1999.
Sun, M. et al. "Intraocular lens alignment from an en face optical coherence tomography image Purkinje-like method", Optical Engineering, Society of Photo-Optical Instrumentation Engineers, vol. 51, No. 6, pp. 061704-1 to 061704-9, Jun. 1, 2014.

\* cited by examiner

SYSTEM AND METHODS FOR COMPENSATING FOR INTRAOCULAR LENS TILT

CROSS-REFERENCE TO RELATED APPLICATION

This application claims priority to U.S. Patent Application No. 63/511,306 filed on Jun. 30, 2023, the content of which is incorporated herein by reference in its entirety.

TECHNICAL FIELD

The present disclosure relates generally to the field of intraocular lenses, and, more specifically, to systems and methods for compensating for intraocular lens (IOL) tilt as part of an IOL adjustment procedure.

BACKGROUND

A cataract is a condition involving the clouding over of the normally clear lens of a subject's eye. Cataracts occur as a result of aging, hereditary factors, trauma, inflammation, metabolic disorders, or exposure to radiation. Age-related cataract is the most common type of cataracts. In treating a cataract, the surgeon removes the native crystalline lens matrix from the subject's capsular bag and replaces it with an intraocular lens (IOL). Traditional IOLs provide one or more selected focal lengths that allow the subject to have distance vision. However, after cataract surgery, subjects with traditional IOLs often require glasses or other corrective eyewear for certain activities since the eye can no longer undertake accommodation (or change its optical power) to maintain a clear image of an object or focus on an object as its distance varies.

Newer IOLs such as accommodating IOLs, allow the eye to regain at least some focusing ability. Accommodating IOLs (AIOLs) use forces available in the eye to change some portion of the optical system in order to refocus the eye on distant or near targets. In addition, there may be a need to adjust AIOLs and non-accommodating IOLs post-operatively or after implantation within the eye of a subject. In some instances, an implanted IOL or AIOL may be adjusted using laser treatments.

However, IOLs or AIOLs may be positioned or oriented in a manner within the eye that makes post-implant adjustment difficult. Therefore, improved solutions which allow a clinician or other medical professional to safely and accurately adjust an AIOL or IOL post-operatively may be beneficial. Such a solution should also be designed with clinical considerations in mind.

SUMMARY

Disclosed herein are systems and methods for compensating for a tilt of an intraocular lens (IOL) and systems and methods for adjusting the IOL. In some embodiments, a method of compensating for a tilt of an intraocular lens (IOL) with optical coherence tomography (OCT) guidance comprises: capturing one or more OCT images of an eye of a subject using an OCT imaging apparatus, wherein the IOL can be implanted within the eye of the subject; generating a fixation target such that the fixation target is visible to the eye of the subject; and moving the fixation target until a transverse plane of the IOL is perpendicular or substantially perpendicular to an optical axis of an ophthalmic system.

In some embodiments, the OCT imaging apparatus can be communicatively coupled to an electronic display and wherein moving the fixation target further comprises moving the fixation target until the transverse plane of the IOL as shown in the one or more OCT images displayed on the electronic display is perpendicular or substantially perpendicular to the optical axis displayed on the electronic display.

In some embodiments, the method can further comprise determining a degree of the tilt of the IOL and moving the fixation target based on the degree of tilt.

In some embodiments, the tilt of the IOL can have a tilt angle between about 4.0 degrees and about 8.0 degrees.

In some embodiments, moving the fixation target can further comprise moving the fixation target in at least one of a medial direction, a lateral direction, an inferior direction, and a superior direction with respect to the subject.

In some embodiments, the optical axis of the ophthalmic system can be a Z-axis of a focusing lens or focusing objective of a laser of the ophthalmic system, and wherein moving the fixation target can further comprise moving the fixation target to a position not axially aligned with the Z-axis.

In some embodiments, the optical axis can be oriented vertically when the subject is lying in a supine position.

In some embodiments, the fixation target can be a fixation light generated by a fixation light source.

In some embodiments, the fixation light can be a beam of light having a wavelength in a visible spectrum.

In some embodiments, the fixation light can be moveable in response to a user input by a user of the ophthalmic system.

In some embodiments, the fixation light source can be configured to be automatically moved by the ophthalmic system.

In some embodiments, the fixation target can be displayed on a target display visible to the subject.

In some embodiments, he fixation target can be a computer-generated graphic.

In some embodiments, the OCT imaging apparatus can be an integrated component of the ophthalmic system.

In some embodiments, a method of adjusting an intraocular lens (IOL) comprises: capturing one or more OCT images of an eye of a subject using an OCT imaging apparatus, wherein the IOL is implanted within the eye of the subject; generating a fixation target such that the fixation target is visible to the eye of the subject; moving the fixation target until a transverse plane of the IOL is perpendicular or substantially perpendicular to an optical axis of an ophthalmic system; and directing a laser beam generated by a laser of the ophthalmic system at the IOL to adjust a base power of the IOL.

In some embodiments, the OCT imaging apparatus can be communicatively coupled to an electronic display, and wherein moving the fixation target further comprises moving the fixation target until the transverse plane of the IOL as shown in the one or more OCT images displayed on the electronic display is perpendicular or substantially perpendicular to the optical axis displayed on the electronic display.

In some embodiments, the method further comprises determining a degree of tilt of the IOL and moving the fixation target based on the degree of tilt.

In some embodiments, the degree of tilt of the IOL can be between about 4.0 degrees and about 8.0 degrees.

In some embodiments, moving the fixation target can further comprise moving the fixation target in at least one of a medial direction, a lateral direction, an inferior direction, and a superior direction with respect to the subject.

In some embodiments, the optical axis of the ophthalmic system can be a Z-axis of a focusing lens or focusing objective of the laser of the ophthalmic system, and wherein moving the fixation target further comprises moving the fixation target to a position not axially aligned with the Z-axis.

In some embodiments, the optical axis can be oriented vertically when the subject is lying in a supine position.

In some embodiments, the fixation target can be a fixation light generated by a fixation light source.

In some embodiments, the fixation light can be a beam of light having a wavelength in a visible spectrum.

In some embodiments, the fixation light can be moveable in response to a user input by a user of the ophthalmic system.

In some embodiments, the fixation light source can be configured to be automatically moved by the ophthalmic system.

In some embodiments, the fixation target can be displayed on a target display visible to the subject.

In some embodiments, the fixation target can be a computer-generated graphic.

In some embodiments, the OCT imaging apparatus can be an integrated component of the ophthalmic system.

In some embodiments, the laser beam can be generated by a femtosecond laser.

In some embodiments, directing the laser beam at the IOL can further comprise directing the laser beam at one or more haptics of the IOL.

In some embodiments, the IOL can be an accommodating IOL.

In some embodiments, the IOL can be a non-accommodating fluid-adjustable IOL.

In some embodiments, an ophthalmic system is disclosed. The ophthalmic system comprises: an optical coherence tomography (OCT) imaging apparatus configured to produce one or more OCT images of an eye of a subject having an intraocular lens (IOL) implanted within the eye; and a fixation target source configured to generate a moveable fixation target that is visible to the eye of the subject, wherein the fixation target is configured to be moved until a transverse plane of the IOL is perpendicular or substantially perpendicular to an optical axis of the ophthalmic system.

In some embodiments, the OCT imaging apparatus can be communicatively coupled to an electronic display, and wherein moving the fixation target further comprises moving the fixation target until the transverse plane of the IOL as shown in the one or more OCT images displayed on the electronic display is perpendicular or substantially perpendicular to the optical axis displayed on the electronic display.

In some embodiments, the ophthalmic system further comprises a laser configured to generate and direct a laser beam at the IOL to adjust a base power of the IOL.

In some embodiments, the optical axis of the ophthalmic system can be a Z-axis of a focusing lens or focusing objective of the laser of the ophthalmic system and wherein the fixation target is configured to be moved to a position not axially aligned with the Z-axis.

In some embodiments, the optical axis can be oriented vertically when the subject is lying in a supine position.

In some embodiments, the laser beam can be generated by a femtosecond laser.

In some embodiments, the ophthalmic system can further comprise a control unit comprising one or more processors coupled to a memory, wherein the one or more processors can be programmed to execute instructions stored on the memory to determine a degree of tilt of the IOL, and wherein the fixation target is configured to be moved based on the degree of tilt.

In some embodiments, the degree of tilt of the IOL can be between about 4.0 degrees and about 8.0 degrees.

In some embodiments, the fixation target can be moveable in at least one of a medial direction, a lateral direction, an inferior direction, and a superior direction with respect to the subject.

In some embodiments, the fixation target can be a fixation light generated by a fixation light source serving as the fixation target source.

In some embodiments, the fixation light can be a beam of light having a wavelength in a visible spectrum.

In some embodiments, the fixation target can be moveable in response to a user input by a user of the ophthalmic system.

In some embodiments, the fixation target can be configured to be automatically moved by the ophthalmic system.

In some embodiments, the fixation target source can be a target display visible to the subject.

In some embodiments, the fixation target can be a computer-generated graphic.

In some embodiments, the OCT imaging apparatus can be an integrated component of the ophthalmic system.

In some embodiments, the IOL can be an accommodating IOL.

In some embodiments, the IOL can be a non-accommodating fluid-adjustable IOL.

DETAILED DESCRIPTION

Figure 1A:
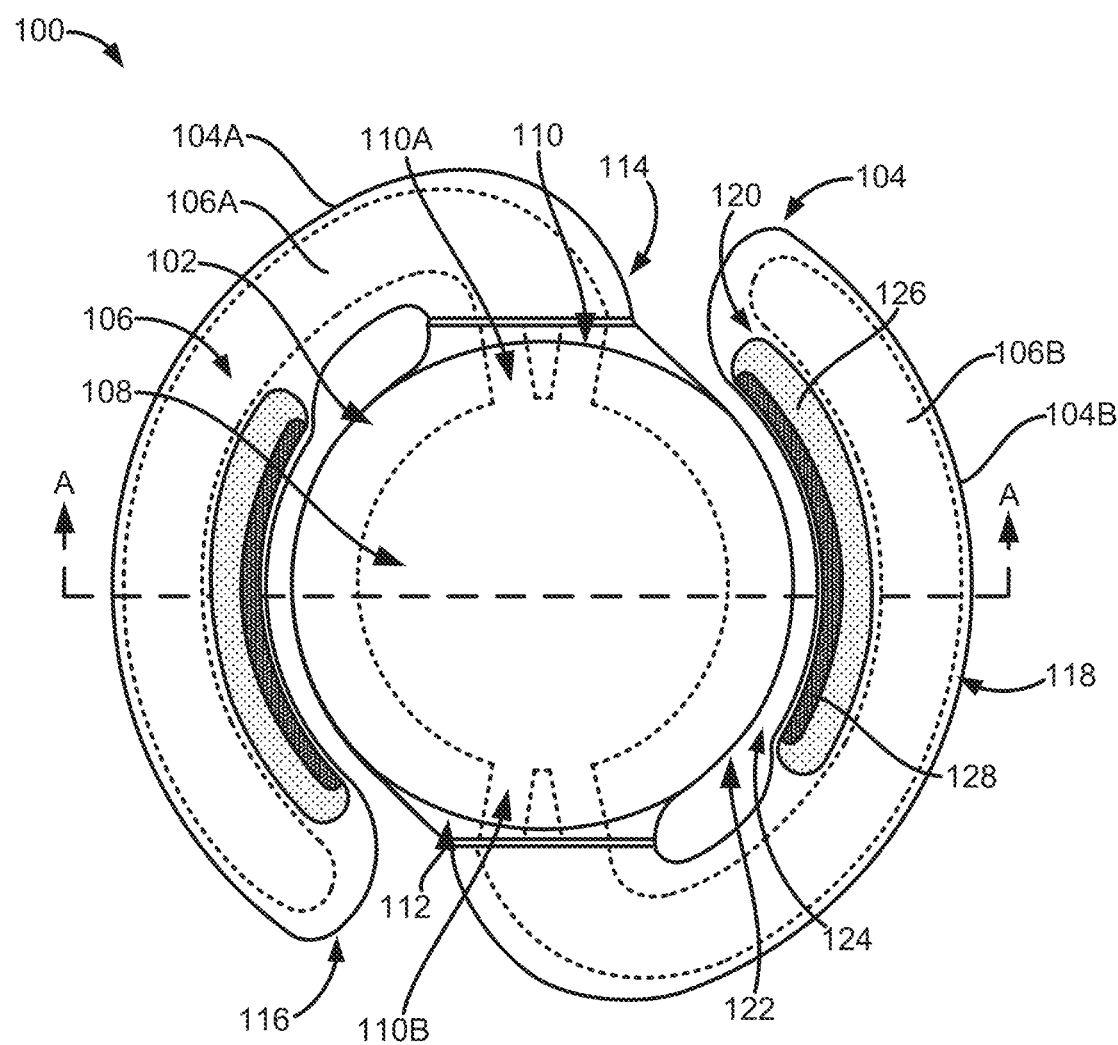
FIG. 1A illustrates a top plan view of one embodiment of an IOL.

FIG. 1A illustrates a top plan view of one embodiment of an adjustable intraocular lens (IOL) 100. For example, the adjustable IOL can be an adjustable accommodating IOL (AIOL). The IOL 100 can be implanted within a subject to correct for defocus aberration, corneal astigmatism, spherical aberration, or a combination thereof. The IOL 100 can comprise an optic portion 102 and one or more haptics 104 including a first haptic 104A and a second haptic 104B coupled to and extending peripherally from the optic portion 102. The IOL 100 can be positioned within a native capsular bag in which a native lens has been removed.

In some embodiments, the haptics 104 can be coupled to and adhered to the optic portion 102. For example, the haptics 104 can be adhered to the optic portion 102 after each is formed separately.

In other embodiments, the IOL 100 can be a one-piece lens such that the haptics 104 are connected to and extend from the optic portion 102. In these embodiments, the haptics 104 are formed along with the optic portion 102 and are not adhered or otherwise coupled to the optic portion 102 in a subsequent step.

The IOL 100 can be implanted within a native capsular bag of a subject after the subject's native lens has been removed. When implanted within the native capsular bag, the optic portion 102 can be adapted to refract light that enters the eye onto the retina. The one or more haptics 104 can be configured to engage the capsular bag and be adapted to deform in response to ciliary muscle movement (e.g., muscle relaxation, muscle contraction, or a combination thereof) in connection with capsular bag reshaping.

Each of the haptics 104 can comprise a haptic fluid lumen 106 extending through at least part of the haptic 104. For example, the first haptic 104A can comprise a first haptic fluid lumen 106A extending through at least part of the first haptic 104A and the second haptic 104B can comprise a second haptic fluid lumen 106B extending through at least part of the second haptic 104B. The haptic fluid lumen 106 (e.g., any of the first haptic fluid lumen 106A or the second haptic fluid lumen 106B) can be in fluid communication with or fluidly connected to an optic fluid chamber 108 within the optic portion 102.

The optic fluid chamber 108 can be in fluid communication with the one or more haptic fluid lumens 106 through one or more fluid channels 110. The fluid channels 110 can be conduits or passageways fluidly connecting the optic fluid chamber 108 to the haptic fluid lumens 106. The fluid channels 110 can be spaced apart from one another. For example, a pair of fluid channels 110 can be spaced apart between about 0.1 mm to about 1.0 mm. In some embodiments, each of the fluid channels 110 can have a diameter of between about 0.4 mm to about 0.6 mm.

The haptics 104 can be coupled to the optic portion 102 at a reinforced portion 112. The reinforced portion 112 can serve as a haptic-optic interface. The pair of fluid channels 110 can be defined or formed within part of the reinforced portion 112.

As shown in FIG. 1A, the optic fluid chamber 108 can be in fluid communication with the first haptic fluid lumen 106A through a first pair of fluid channels 110A. The optic fluid chamber 108 can also be in fluid communication with the second haptic fluid lumen 106B through a second pair of fluid channels 110B.

In some embodiments, the first pair of fluid channels 110A and the second pair of fluid channels 110B can be positioned substantially on opposite sides of the optic portion 102. The first pair of fluid channels 110A can be positioned substantially diametrically opposed to the second pair of fluid channels 110B. The first pair of fluid channels 110A and the second pair of fluid channels 110B can be defined or extend through part of the optic portion 102. The first pair of fluid channels 110A and the second pair of fluid channels 110B can be defined or extend through a posterior element 132 of the optic portion 102 (see, e.g., FIGS. 1B-1E).

FIG. 1A also illustrates that each of the haptics 104 (e.g., any of the first haptic 104A or the second haptic 104B) can have a proximal attachment end 114 and a distal free end 116. A haptic fluid port 152 (see, e.g., FIG. 1E) can be defined at the proximal attachment end 114 of the haptic 104. The haptic fluid port 152 can serve as an opening of the haptic fluid lumen 106. Fluid within the haptic fluid lumen 106 can flow out of the haptic fluid lumen 106 through the haptic fluid port 152 and into the optic fluid chamber 108 via the fluid channels 110 when the haptic 104 is coupled to the optic portion 102. Similarly, fluid within the optic fluid chamber 108 can flow out of the optic fluid chamber 108 through the pair of fluid channels 110 and into the haptic fluid lumen 106 through the haptic fluid port 152.

Each of the haptics 104 can comprise a radially-outer haptic lumen wall 118 and a radially-inner haptic lumen wall 120. The radially-outer haptic lumen wall 118 (also referred to as a radially-outer lateral wall of the haptic 104) can be configured to face and contact an inner surface of a patient's capsular bag when the IOL 100 is implanted within the capsular bag. The radially-inner haptic lumen wall 120 (also referred to as a radially-inner lateral wall of the haptic 104) can be configured to face an outer peripheral surface 122 of the optic portion 102.

As previously discussed, the IOL 100 can be implanted or introduced into a patient's capsular bag after a native lens has been removed from the capsular bag. The patient's capsular bag is connected to zonule fibers which are connected to the patient's ciliary muscles. The capsular bag is elastic and ciliary muscle movements can reshape the capsular bag via the zonule fibers. For example, when the ciliary muscles relax, the zonules are stretched. This stretching pulls the capsular bag in the generally radially outward direction due to radially outward forces. This pulling of the capsular bag causes the capsular bag to elongate, creating room within the capsular bag. When the patient's native lens is present in the capsular bag, the native lens normally becomes flatter (in the anterior-to-posterior direction), which reduces the power of the lens, allowing for distance vision. In this configuration, the patient's native lens is said to be in a disaccommodated state or undergoing disaccommodation.

When the ciliary muscles contract, however, as occurs when the eye is attempting to focus on near objects, the radially inner portion of the muscles move radially inward, causing the zonules to slacken. The slack in the zonules allows the elastic capsular bag to contract and exert radially inward forces on a lens within the capsular bag. When the patient's native lens is present in the capsular bag, the native lens normally becomes more curved (e.g., the anterior part of the lens becomes more curved), which gives the lens more power, allowing the eye to focus on near objects. In this configuration, the patient's native lens is said to be in an accommodated state or undergoing accommodation.

In embodiments where the IOL 100 is an AIOL, the radially-outer haptic lumen wall 118 of the implanted AIOL can directly engage with or be in physical contact with the portion of the capsular bag that is connected to the zonules or zonule fibers. Therefore, the radially-outer haptic lumen wall 118 of the AIOL can be configured to respond to capsular bag reshaping forces that are applied radially when the zonules relax and stretch as a result of ciliary muscle movements.

For example, when the ciliary muscles contract, the peripheral region of the elastic capsular bag reshapes and applies radially inward forces on the radially-outer haptic lumen wall 118 of each of the haptics 104. When the IOL 100 is an AIOL, the radially-outer haptic lumen wall 118 can deform or otherwise change shape and this deformation or shape-change can cause the volume of the haptic fluid lumen 106 to decrease. When the volume of the haptic fluid lumen 106 decreases, the fluid within the haptic fluid lumen 106 is moved or pushed into the optic fluid chamber 108. The optic portion 102 of the AIOL can change shape in response to fluid entering the optic fluid chamber 108 from the haptic fluid lumen 106. This can increase the base power or base spherical power of the AIOL and allow a patient with the AIOL implanted within the eye of the patient to focus on near objects. In this state, the adjustable AIOL can be considered to have undergone accommodation.

When the ciliary muscles relax, the peripheral region of the elastic capsular bag is stretched radially outward and the capsular bag elongates and more room is created within the capsular bag. The radially-outer haptic lumen wall 118 of the haptics 104 can be configured to respond to this capsular bag reshaping by returning to its non-deformed or non-stressed configuration. This causes the volume of the haptic fluid lumen 106 to increase or return to its non-deformed volume. This increase in the volume of the haptic fluid lumen 106 can cause the fluid within the optic fluid chamber 108 to be drawn out or otherwise flow out of the optic fluid chamber 108 and back into the haptic fluid lumen 106. Fluid moves out of the optic fluid chamber 108 into the haptic fluid lumen 106 through the same fluid channels 110 formed within the optic portion 102.

The optic portion 102 of the AIOL can change shape in response to fluid exiting the optic fluid chamber 108 and into the haptic fluid lumen 106. This can decrease the base power or base spherical power of the AIOL and allow a patient with the AIOL implanted within the eye of the patient to focus on distant objects or provide for distance vision. In this state, the AIOL can be considered to have undergone disaccommodation.

Figure 1B:
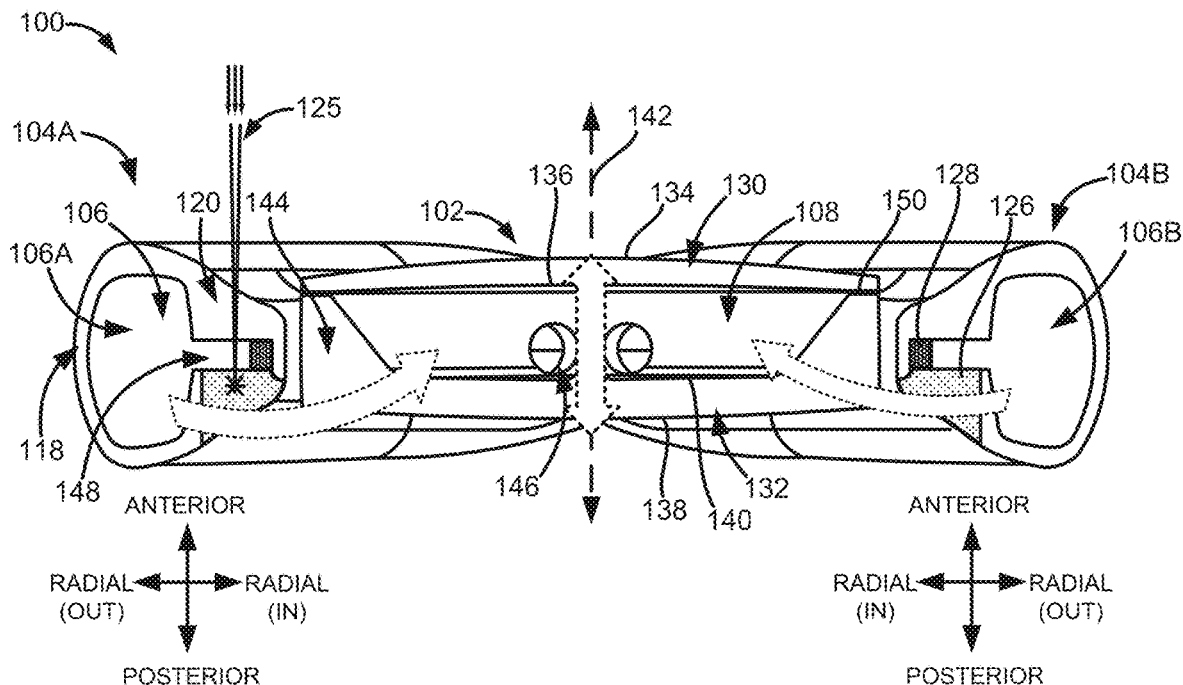
FIGS. 1B and 1C illustrate cross-sectional views of the IOL of FIG. 1A taken along cross-section A-A.
Figure 1C:
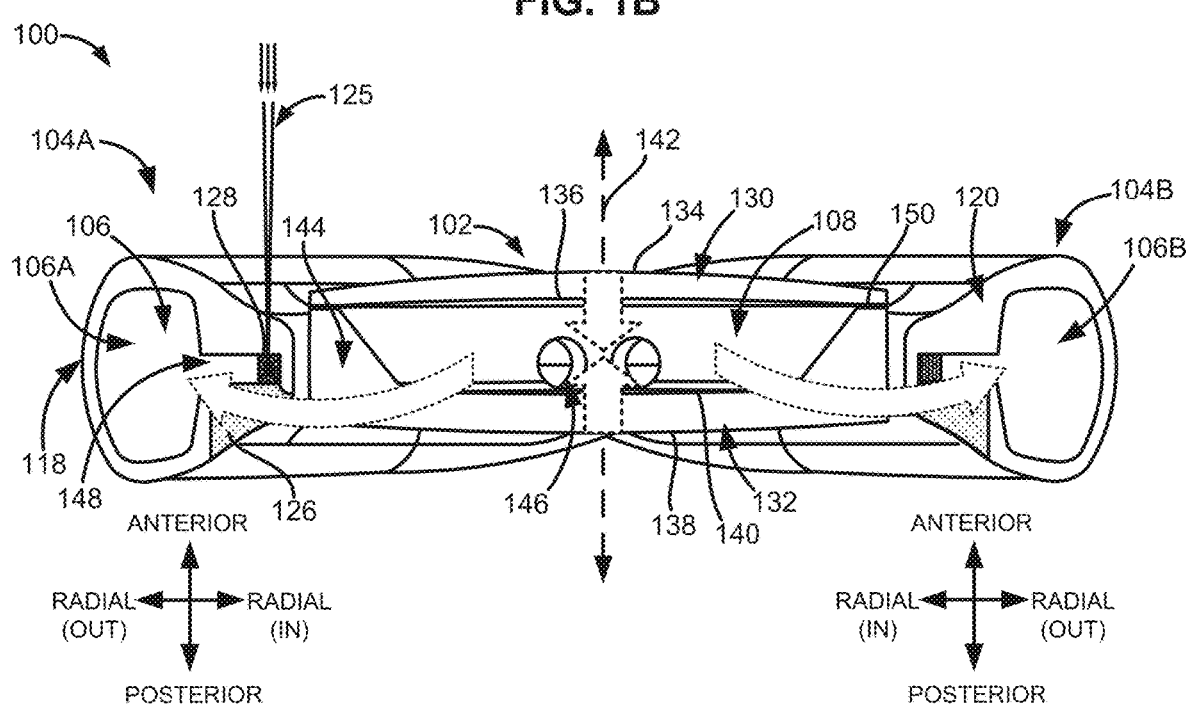
Figure 1D:
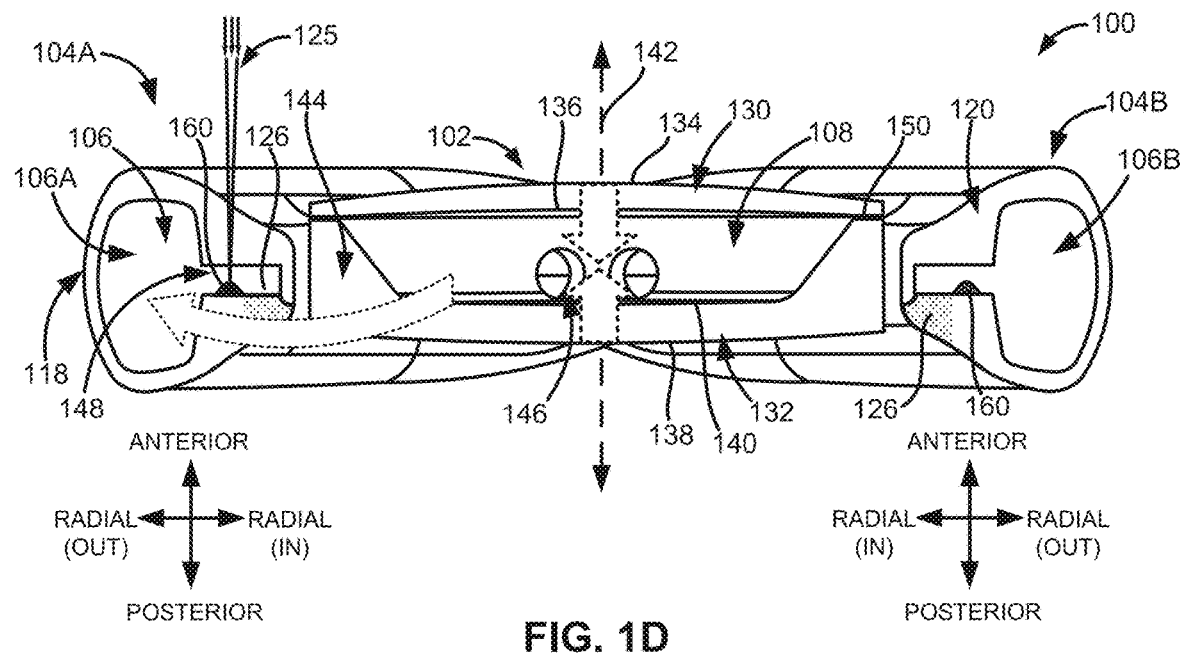
FIG. 1D illustrates a cross-sectional view of another embodiment of the IOL.

When the IOL 100 is an AIOL, the radially-outer haptic lumen walls 118 of the haptics 104 can be made thinner than the radially-inner haptic lumen walls 120 to allow the haptics 104 to maintain a high degree of sensitivity to radial forces applied to an equatorial region of the haptics 104 by capsular bag reshaping as a result of ciliary muscle movements. As shown in FIGS. 1B-1D, the radially-inner haptic lumen walls 120 of the haptics 104 can be designed to be thicker or bulkier than the radially-outer haptic lumen walls 118 to provide the haptics 104 with stiffness or resiliency in the anterior-to-posterior direction. In certain embodiments, the radially-inner haptic lumen wall 120 can taper in shape as the radially-inner haptic lumen wall 120 gets closer to the optic portion 102. When designed in this manner, the haptics 104 can be less sensitive to capsular bag forces applied in the anterior-to-posterior direction. For example, when capsular bag forces are applied to the haptics 104 in the anterior-to-posterior direction, less fluid movement occurs between the haptic fluid lumens 106 and the optic fluid chamber 108 than when forces are applied in the radial direction. Since less fluid movement occurs, less changes in the base power of the AIOL occur.

Although AIOLs are depicted and described in this disclosure, any reference to an AIOL can also refer to one of the AIOLs discussed and depicted in the following U.S. publications: U.S. Pat. Pub. No. 2021/0100652; U.S. Pat. Pub. No. 2021/0100650; U.S. Pat. Pub. No. 2020/0337833; and U.S. Pat. Pub. No. 2018/0153682; and in the following issued U.S. Pat. Nos. 11,426,270; 10,433,949; 10,299,913; 10,195,020; and 8,968,396, the contents of which are incorporated herein by reference in their entireties.

Moreover, although FIGS. 1A-1E illustrate the IOL 100 as an AIOL, it is contemplated by this disclosure that the IOL 100 can also be a non-accommodating adjustable IOL (also referred to as a static-focus adjustable IOL). Examples of non-accommodating or static-focus adjustable IOLs are discussed in U.S. Pat. No. 11,471,272, the content of which is incorporated herein by reference in its entirety.

In some embodiments, the IOL 100 can be designed such that a gap 124 or void space radially separates the radially-inner haptic lumen wall 120 of the haptic 104 from the outer peripheral surface 122 of the optic portion 102. This can allow portion(s) of the haptic 104 to change shape in response to an external energy such as a laser light 125 (see, e.g., FIGS. 1B-1D) directed at the haptic 104.

FIG. 1A also illustrates that one or more portions of each of the haptics 104 can be made of a composite material. As will be discussed in more detail in later sections, the composite material can comprise or be made in part of an energy absorbing constituent, a plurality of expandable components or shrinkable components, and a cross-linked copolymer used to make the rest of the haptic 104. The portions of the haptics 104 made of the composite material can be configured to expand or shrink in response to the laser light 125 (see, e.g., FIGS. 1B-1D) directed at the composite material. Depending on where the composite material is positioned or integrated within each of the haptics 104, the composite material can act as a lumen filler 126 to take up space within the haptic fluid lumen 106, a lumen expander 128 to create more space within the haptic fluid lumen 106, or a shrinkable portion to free up space in a lumen or cavity.

As will be discussed in more detail in later sections, when laser light 125 is applied to the composite material configured as the lumen filler 126, the composite material can expand and the expansion of the composite material in this instance can decrease a volume of the haptic fluid lumen 106 and cause fluid within the haptic fluid lumen 106 to be displaced into the optic fluid chamber 108. This can cause the optic portion 102 to change shape (e.g., cause the anterior or posterior elements of the optic portion 102 to become more curved) leading to an increase in the base power of the optic portion 102.

Alternatively, when the laser light 125 is applied to the composite material configured as the lumen expander 128, the composite material can expand and the expansion of the composite material in this instance can increase a volume of the haptic fluid lumen 106 and cause fluid within the optic fluid chamber 108 to be drawn into the haptic fluid lumen 106. This can also cause the optic portion 102 to change shape (e.g., cause the anterior or posterior elements of the optic portion 102 to become less curved or flatter) leading to a decrease in the base power of the optic portion 102.

In yet another embodiment, when the laser light 125 is applied to the composite material configured as a shrinkable portion, the shrinkable portion can shrink or decrease in size and the shrinkage or contraction of the shrinkable portion can increase a volume of the haptic fluid lumen 106 and cause fluid within the optic fluid chamber 108 to be drawn into the haptic fluid lumen 106. This can also cause the optic portion 102 to change shape (e.g., cause the anterior or posterior elements of the optic portion 102 to become less curved or flatter) leading to a decrease in the base power of the optic portion 102.

One technical problem faced by the applicants is that once an IOL 100 is implanted within a capsular bag of a patient, an aggressive healing response by tissue within the capsular bag can squeeze or contract the optic portion 102 of the lens and drive the optical power higher than initially anticipated. Another technical problem faced by the applicants is that the pre-operative biometry measurements made on a patient's eye may be incorrect, leading to lenses with the wrong lens power being prescribed and implanted within the patient. Moreover, yet another technical problem faced by the applicants is that a patient's cornea or muscles within the eye may change as a result of injury, disease, or aging. One technical solution discovered and developed by the applicants is to design an IOL 100 that can be adjusted post-operatively (i.e., post-implantation) to account for such changes or errors.

FIGS. 1B and 1C illustrate cross-sectional views of the IOL 100 of FIG. 1A taken along cross-section A-A. As shown in FIGS. 1B and 1C, the optic portion 102 can comprise an anterior element 130 and a posterior element 132. The fluid-filled optic fluid chamber 108 can be defined in between the anterior element 130 and the posterior element 132.

The anterior element 130 can comprise an anterior optical surface 134 and an anterior inner surface 136 opposite the anterior optical surface 134. The posterior element 132 can comprise a posterior optical surface 138 and a posterior inner surface 140 opposite the posterior optical surface 138. Any of the anterior optical surface 134, the posterior optical surface 138, or a combination thereof can be considered and referred to as an external optical surface. The anterior inner surface 136 and the posterior inner surface 140 can face the optic fluid chamber 108. At least part of the anterior inner surface 136 and at least part of the posterior inner surface 140 can serve as chamber walls of the optic fluid chamber 108.

As shown in FIGS. 1B and 1C, the optic portion 102 can have a lens optical axis 142 extending in an anterior-to-posterior direction through a center of the optic portion 102. The lens optical axis 142 can extend through the centers of both the anterior element 130 and the posterior element 132.

The thickness of the anterior element 130 can be greater at or near the lens optical axis 142 than at the periphery of the anterior element 130. In some embodiments, the thickness of the anterior element 130 can increase gradually from the periphery of the anterior element 130 toward the lens optical axis 142.

In certain embodiments, the thickness of the anterior element 130 at or near the lens optical axis 142 can be between about 0.45 mm and about 0.55 mm. In these and other embodiments, the thickness of the anterior element 130 near the periphery can be between about 0.20 mm and about 0.40 mm. Moreover, the anterior inner surface 136 of the anterior element 130 can have less curvature or be flatter than the anterior optical surface 134.

The thickness of the posterior element 132 can be greater at or near the lens optical axis 142 than portions of the posterior element 132 radially outward from the lens optical axis 142 but prior to reaching a raised periphery 144 of the posterior element 132. The thickness of the posterior element 132 can gradually decrease from the lens optical axis 142 to portions radially outward from the lens optical axis 142 (but prior to reaching the raised periphery 144). As shown in FIGS. 1B and 1C, the thickness of the posterior element 132 can increase once again from a radially inner portion of the raised periphery 144 to a radially outer portion of the raised periphery 144.

In certain embodiments, the thickness of the posterior element 132 at or near the lens optical axis 142 can be between about 0.45 mm and about 0.55 mm. In these and other embodiments, the thickness of the posterior element 132 radially outward from the lens optical axis 142 (but prior to reaching the raised periphery 144) can be between about 0.20 mm and about 0.40 mm. The thickness of the posterior element 132 near the radially outer portion of the raised periphery 144 can be between about 1.00 mm and 1.15 mm. Moreover, the posterior inner surface 140 of the posterior element 132 can have less curvature or be flatter than the posterior optical surface 138.

The optic portion 102 can have a base power or base spherical power. The base power of the optic portion 102 can be configured to change based on an internal fluid pressure within the fluid-filled optic fluid chamber 108. The base power of the optic portion 102 can be configured to increase or decrease as fluid enters or exits the fluid-filled optic fluid chamber 108.

The base power of the optic portion 102 can be configured to increase as fluid enters the fluid-filled optic fluid chamber 108 from the haptic fluid lumen(s) 106, as depicted in FIG. 1B using the curved broken-line arrows. For example, the anterior element 130 of the optic portion 102 can be configured to increase its curvature in response to the fluid entering the optic fluid chamber 108. Also, for example, the posterior element 132 of the optic portion 102 can be configured to increase its curvature in response to the fluid entering the optic fluid chamber 108. In further embodiments, both the anterior element 130 and the posterior element 132 can be configured to increase their curvatures in response to the fluid entering the optic fluid chamber 108.

The base power of the optic portion 102 can be configured to decrease as fluid exits or is drawn out of the fluid-filled optic fluid chamber 108 into the haptic fluid lumen(s) 106, as depicted in FIG. 1C using the curved broken-line arrows. For example, the anterior element 130 of the optic portion 102 can be configured to decrease its curvature (or flatten out) in response to the fluid exiting the optic fluid chamber 108. Also, for example, the posterior element 132 of the optic portion 102 can be configured to decrease its curvature (or flatten out) in response to the fluid exiting the optic fluid chamber 108. In further embodiments, both the anterior element 130 and the posterior element 132 can be configured to decrease their curvatures in response to the fluid exiting the optic fluid chamber 108.

It should be noted that although FIGS. 1B and 1C illustrate the fluid entering and exiting the optic fluid chamber 108 from the haptic fluid lumens 106 using the curved broken-line arrows, fluid enters and exits the optic fluid chamber 108 via the fluid channels 110 and apertures 146 defined along the posterior element 132. The apertures 146 can be holes or openings defined along the posterior element 132 that serve as terminal ends of the fluid channels 110. When the IOL 100 comprises a pair of fluid channels 110, the pair of apertures 146 serving as ends of the fluid channels 110 can be spaced apart from one another between about 0.1 mm to about 1.0 mm.

As shown in FIGS. 1B and 1C, one or more portions of the IOL 100 can be made of a composite material designed to respond to an external energy, such as laser light 125, applied to the composite material. For example, one or more portions of each of the haptics 104 of the IOL 100 can be made of the composite material.

Depending on where the composite material is positioned or integrated within each of the haptics 104 and the composition of the composite material, the composite material can act as a lumen filler 126, a lumen expander 128, or a shrinkable portion.

For example, the lumen filler 126 can be a portion of the haptic 104 made of the composite material that is designed to decrease a volume of the haptic fluid lumen 106 in response to an external energy (e.g., laser light 125) directed at the lumen filler 126. The lumen expander 128 can be a portion of the haptic 104 made of the composite material that is designed to increase a volume of the haptic fluid lumen 106 in response to an external energy (e.g., laser light 125) directed at the lumen expander 128.

As shown in FIGS. 1B and 1C, each of the haptics 104 can comprise a channel 148. The channel 148 can be defined within part of the radially-inner haptic lumen wall 120. For example, the channel 148 can extend partially into the radially-inner haptic lumen wall 120. The channel 148 can be in fluid communication with the haptic fluid lumen 106 or be considered part of the haptic fluid lumen 106.

In some embodiments, the lumen filler 126 can be positioned posterior to the channel 148. In these embodiments, the lumen filler 126 can replace or act as the posterior portion of the radially-inner haptic lumen wall 120. The lumen filler 126 can also be positioned radially inward of the portion of the haptic fluid lumen 106 that is not the channel 148.

At least part of the lumen filler 126 can be in fluid communication with the channel 148. For example, at least part of an anterior portion or layer of the lumen filler 126 can be in fluid communication with or otherwise exposed to the channel 148.

As shown in FIGS. 1B and 1C, in some embodiments, a radially outer lateral side of the lumen filler 126 is not in fluid communication with the haptic fluid lumen 106. In these embodiments, the radially outer lateral side of the lumen filler 126 is separated from the haptic fluid lumen 106 by a part of the haptic 104 not made of the composite material.

The lumen expander 128 can be positioned radially inward of the channel 148. The lumen expander 128 can also be positioned anterior to the lumen filler 126. More specifically, for example, the lumen expander 128 can be positioned anterior to a radially inner portion of the lumen filler 126.

In some embodiments, the lumen expander 128 can be positioned within the channel 148. In these embodiments, the lumen expander 128 can be positioned at a radially innermost end of the channel 148. For example, the radially-inner haptic lumen wall 120 can taper in shape as the radially-inner haptic lumen wall 120 gets closer to the optic portion 102. The lumen expander 128 can be positioned at a radially innermost end of the channel 148 near the tapered end of the radially-inner haptic lumen wall 120.

As shown in FIGS. 1B and 1C, a radially outer lateral side of the lumen expander 128 can be in fluid communication with the channel 148 and the haptic fluid lumen 106. In some embodiments, the lumen expander 128 does not extend all the way to the radially inner-most part of the radially-inner haptic lumen wall 120. In these embodiments, a part of the haptic 104 that is not made of the composite material can serve as the radially inner-most part of the radially-inner haptic lumen wall 120 and separate the lumen expander 128 from the outer peripheral surface 122 of the optic portion 102.

In some embodiments, the lumen expander 128 can be connected or otherwise coupled to the lumen filler 126. In these and other embodiments, the lumen expander 128 and the lumen filler 126 can be or refer to different parts of the same composite material. For example, the lumen filler 126 can be shaped substantially as a curved cornice and the lumen expander 128 can be shaped substantially as a rectangular cuboid extending from an anterior surface of the cornice.

It should be understood by one of ordinary skill in the art that even though different colored shading is used to differentiate the lumen filler 126 from the lumen expander 128 in the figures (that is, a darker shading pattern is used to depict the lumen expander 128 and a lighter shading pattern is used to depict the lumen filler 126), both the lumen filler 126 and the lumen expander 128 can be made of the same composite material or refer to different parts/features of the same block of composite material.

In other embodiments, the lumen filler 126 and the lumen expander 128 can be made of different types of composite materials. In these embodiments, the lumen filler 126 can be made of a first type of composite material and the lumen expander 128 can be made of a second type of composite material. In certain embodiments, the lumen filler 126 and the lumen expander 128 can be made of different colored composite materials. For example, the composite material can comprise an energy absorbing constituent such as an energy absorbing pigment or dye.

As a more specific example, either the lumen filler 126 or the lumen expander 128 can be made of a composite material comprising a black-colored energy absorbing pigment such as graphitized carbon black. In this example, if one of the lumen filler 126 or the lumen expander 128 is made of a composite material comprising graphitized carbon black, the other can be made of another type of composite material comprising a red-colored energy absorbing pigment such as an azo dye (e.g., Disperse Red 1 dye).

As shown in FIG. 1B, an external energy such as laser light 125 can be directed at the lumen filler 126 to cause at least part of the lumen filler 126 to expand and grow in size. For example, this expansion can manifest itself as a protuberance growing or jutting out of the lumen filler 126. For example, when laser light 125 is directed at the anterior portion or layer of the lumen filler 126 in fluid communication with or otherwise exposed to the channel 148, a protuberance can grow out of the anterior portion and into the channel 148. Since the channel 148 is in fluid communication with the haptic fluid lumen 106 (or is considered part of the haptic fluid lumen 106), the volume of the haptic fluid lumen 106 can decrease in response to the formation of the protuberance. This can cause fluid within the haptic fluid lumen 106 to be pushed or otherwise displaced into the optic fluid chamber 108. As a result, at least one of the anterior element 130 and the posterior element 132 can increase its curvature and the base power of the optic portion 102 can increase in response to the laser stimulus directed at the lumen filler 126.

An external energy such as the laser light 125 (e.g., laser pulses) can be directed at the lumen expander 128 to cause at least part of the lumen expander 128 to expand and grow in size. As will be discussed in more detail in later sections, this expansion can manifest itself as an expansion of the channel 148. For example, when laser light 125 is directed at the lumen expander 128, the lumen expander 128 can grow in size and enlarge the channel 148. Since the channel 148 is in fluid communication with the haptic fluid lumen 106 (or is considered part of the haptic fluid lumen 106), the volume of the haptic fluid lumen 106 can increase in response to the growth of the lumen expander 128. This can cause fluid within the haptic fluid lumen 106 to be drawn out of the optic fluid chamber 108 and into the haptic fluid lumen 106. As a result, at least one of the anterior element 130 and the posterior element 132 can decrease its curvature and the base power of the optic portion 102 can decrease in response to the laser light 125 (e.g., laser pulses) directed at the lumen expander 128.

FIG. 1D illustrates a cross-sectional view of another embodiment of the IOL 100 comprising a shrinkable portion 160 made of a different type of composite material. In some embodiments, the shrinkable portion 160 can be adhered or otherwise coupled to a part of the radially-inner haptic lumen wall 120 of each of the haptics 104. As shown in FIG. 1D, the shrinkable portion 160 can be adhered or otherwise coupled to a part of a posterior portion of the radially-inner haptic lumen wall 120. In other embodiments not shown in the figures, the shrinkable portion 160 can be adhered or otherwise coupled to a part of an anterior portion of the radially-inner haptic lumen wall 120.

The shrinkable portion 160 can be located partly within the channel 148 formed along the radially-inner haptic lumen wall 120 of each of the haptics 104. The shrinkable portion 160 can take up space within the channel 148 prior to being exposed to the external energy.

In other embodiments, at least part of the radially-inner haptic lumen wall 120 can be made of the composite material. For example, at least part of the posterior or anterior portion of the radially-inner haptic lumen wall 120 can be made of the composite material.

The shrinkable portion 160 can shrink or decrease in size in response to the laser light 125 (e.g., laser pulses) directed at the shrinkable portion 160. Since the shrinkable portion 160 formerly takes up space within the channel 148, reducing the size of the shrinkable portion 160 can increase the space available within the channel 148. Moreover, since the channel 148 is in fluid communication with the haptic fluid lumen 106, when the shrinkable portion 160 decreases in size, the volume of the haptic fluid lumen 106 can increase. This can allow fluid within the optic fluid chamber 108 to be drawn into the haptic fluid lumen 106. As a result, at least one of the anterior element 130 and the posterior element 132 can decrease its curvature and the base power of the optic portion 102 can decrease in response to the laser light 125 directed at the shrinkable portion 160 made of the composite material.

The shrinkable portion 160 can initially be a mass extending into the channel 148. The volume of the mass can decrease in response to the external energy directed at the shrinkable portion 160. When the volume of the mass decreases, the volume of available space within the channel 148 and the volume of the haptic fluid lumen 106 can increase, thereby drawing fluid out of the optic fluid chamber 108 and into the haptic fluid lumen 106.

The base power of the optic portion 102 can be configured to decrease as fluid exits or is drawn out of the fluid-filled optic fluid chamber 108 into the haptic fluid lumen(s) 106, as depicted in FIG. 1D. For example, the anterior element 130 of the optic portion 102 can be configured to decrease its curvature (or flatten out) in response to the fluid exiting the optic fluid chamber 108. Also, for example, the posterior element 132 of the optic portion 102 can be configured to decrease its curvature (or flatten out) in response to the fluid exiting the optic fluid chamber 108. In further embodiments, both the anterior element 130 and the posterior element 132 can be configured to decrease their curvatures in response to the fluid exiting the optic fluid chamber 108.

In some embodiments, the fluid within the optic fluid chamber 108 and the haptic fluid lumen(s) 106 can be an oil. More specifically, in certain embodiments, the fluid within the optic fluid chamber 108 and the haptic fluid lumen(s) 106 can be a silicone oil or fluid. For example, the fluid can be a silicone oil made in part of a diphenyl siloxane. In other embodiments, the fluid can be a silicone oil made in part of a ratio of two dimethyl siloxane units to one diphenyl siloxane unit. More specifically, in some embodiments, the fluid can be a silicone oil made in part of diphenyltetramethyl cyclotrisiloxane or a copolymer of diphenyl siloxane and dimethyl siloxane. In further embodiments, the fluid can be a silicone oil comprising branched polymers.

The fluid (e.g., the silicone oil) can be index matched with a lens body material used to make the optic portion 102. When the fluid is index matched with the lens body material, the entire optic portion 102 containing the fluid can act as a single lens. For example, the fluid can be selected so that it has a refractive index of between about 1.48 and 1.53 (or between about 1.50 and 1.53). In some embodiments, the fluid (e.g., the silicone oil) can have a polydispersity index of between about 1.2 and 1.3. In other embodiments, the fluid (e.g., the silicone oil) can have a polydispersity index of between about 1.3 and 1.5. In other embodiments, the fluid (e.g., the silicone oil) can have a polydispersity index of between about 1.1 and 1.2. Other example fluids are described in U.S. Patent Publication No. 2018/0153682, which is herein incorporated by reference in its entirety.

The optic portion 102 can be made in part of a deformable or flexible material. In some embodiments, the optic portion 102 can be made in part of a deformable or flexible polymeric material. For example, the anterior element 130, the posterior element 132, or a combination thereof can be made in part of a deformable or flexible polymeric material. The one or more haptics 104 (e.g., the first haptic 104A, the second haptic 104B, or a combination thereof) can be made in part of the same deformable or flexible material as the optic portion 102. In other embodiments, the one or more haptics 104 can be made in part of different materials from the optic portion 102.

In some embodiments, the optic portion 102 can comprise or be made in part of a lens body material. The lens body material can be made in part of a cross-linked copolymer comprising a copolymer blend. The copolymer blend can comprise an alkyl acrylate or methacrylate, a fluoro-alkyl (meth)acrylate, and a phenyl-alkyl acrylate. It is contemplated by this disclosure and it should be understood by one of ordinary skill in the art that these types of acrylic cross-linked copolymers can be generally copolymers of a plurality of acrylates, methacrylates, or a combination thereof and the term "acrylate" as used herein can be understood to mean acrylates, methacrylates, or a combination thereof interchangeably unless otherwise specified. The cross-linked copolymer used to make the lens body material can comprise an alkyl acrylate in the amount of about 3% to 20% (wt %), a fluoro-alkyl acrylate in the amount of about 10% to 35% (wt %), and a phenyl-alkyl acrylate in the amount of about 50% to 80% (wt %). In some embodiments, the cross-linked copolymer can comprise or be made in part of an n-butyl acrylate as the alkyl acrylate, trifluoroethyl methacrylate as the fluoro-alkyl acrylate, and phenylethyl acrylate as the phenyl-alkyl acrylate. More specifically, the cross-linked copolymer used to make the lens body material can comprise n-butyl acrylate in the amount of about 3% to 20% (wt %) (e.g., between about 12% to 16%), trifluoroethyl methacrylate in the amount of about 10% to 35% (wt %) (e.g., between about 17% to 21%), and phenylethyl acrylate in the amount of about 50% to 80% (wt %) (e.g., between about 64% to 67%).

The final composition of the cross-linked copolymer used to make the lens body material can also comprise a cross-linker or cross-linking agent such as ethylene glycol dimethacrylate (EGDMA). For example, the final composition of the cross-linked copolymer used to make the lens body material can also comprise a cross-linker or cross-linking agent (e.g., EGDMA) in the amount of about 1.0%. The final composition of the cross-linked copolymer used to make the lens body material can also comprise an initiator or initiating agent (e.g., Perkadox 16) and a UV absorber.

The one or more haptics 104 can comprise or be made in part of a haptic material. The haptic material can comprise or be made in part of a cross-linked copolymer comprising a copolymer blend. The copolymer blend can comprise an alkyl acrylate, a fluoro-alkyl acrylate, and a phenyl-alkyl acrylate. For example, the cross-linked copolymer used to make the haptic material can comprise an alkyl acrylate in the amount of about 10% to 25% (wt %), a fluoro-alkyl acrylate in the amount of about 10% to 35% (wt %), and a phenyl-alkyl acrylate in the amount of about 50% to 80% (wt %). In some embodiments, the cross-linked copolymer used to make the haptic material can comprise n-butyl acrylate in the amount of about 10% to 25% (wt %) (e.g., between about 19% to about 23%), trifluoroethyl methacrylate in the amount of about 10% to 35% (wt %) (e.g., between about 14% to about 18%), and phenylethyl acrylate in the amount of about 50% to 80% (wt %) (e.g., between about 58% to about 62%). The final composition of the cross-linked copolymer used to make the haptic material can also comprise a cross-linker or cross-linking agent, such as EGDMA, in the amount of about 1.0%. The final composition of the cross-linked copolymer used to make the haptic material can also comprise a number of photoinitiators or photoinitiating agents (e.g., camphorquinone, 1-phenyl-1,2-propanedione, and 2-ethylhexyl-4-(dimenthylamino)benzoate).

In some embodiments, the refractive index of the lens body material can be between about 1.48 and about 1.53. In certain embodiments, the refractive index of the lens body material can be between about 1.50 and about 1.53 (e.g., about 1.5178).

The anterior element 130 can be attached or otherwise adhered to the posterior element 132 via adhesives 150 or an adhesive layer. The adhesive layer can be substantially annular-shaped. The adhesives 150 or adhesive layer can be positioned at a peripheral edge of the optic portion 102 in between the anterior element 130 and the posterior element 132. For example, the adhesives 150 can be positioned on top of the raised periphery 144 of the posterior element 132.

The adhesives 150 or adhesive layer can comprise or be made in part of a biocompatible adhesive. The adhesives 150 or adhesive layer can comprise or be made in part of a biocompatible polymeric adhesive.

The adhesives 150 or adhesive layer can comprise or be made in part of a cross-linkable polymer precursor formulation. The cross-linkable polymer precursor formulation can comprise or be made in part of a copolymer blend, a hydroxyl-functional acrylic monomer, and a photoinitiator.

The copolymer blend can comprise an alkyl acrylate (e.g., n-butyl acrylate in the amount of about 41% to about 45% (wt %)), a fluoro-alkyl acrylate (e.g., trifluoroethyl methacrylate in the amount of about 20% to about 24% (wt %)), and a phenyl-alkyl acrylate (phenylethyl acrylate in the amount of about 28% to about 32% (wt %)). The hydroxyl-functional acrylic monomer can be 2-hydroxyethyl acrylate (HEA). The photoinitiator can be used to facilitate curing of the adhesive. For example, the photoinitiator can be Darocur 4265 (a 50/50 blend of diphenyl(2,4,6-trimethylbenzoyl) phosphine oxide and 2-hydroxy2-methylpropiophenone).

In some embodiments, the same adhesives 150 used to bond the anterior element 130 to the posterior element 132 can also be used to bond or affix the one or more haptics 104 to the optic portion 102.

Figure 1E:
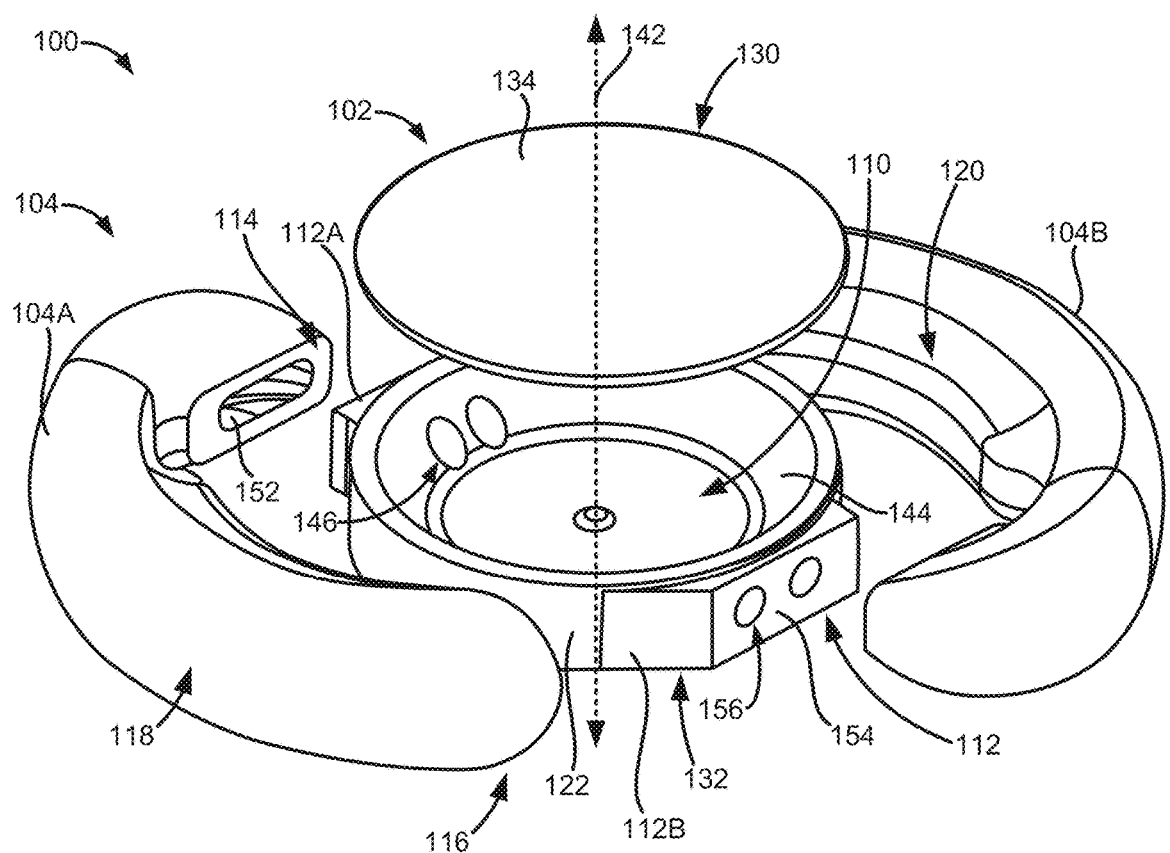
FIG. 1E illustrates an exploded view of the IOL.

FIG. 1E also illustrates that each of the haptics 104 (e.g., any of the first haptic 104A or the second haptic 104B) can have a proximal attachment end 114 and a closed distal free end 116. A haptic fluid port 152 can be defined at the proximal attachment end 114 of the haptic 104. The haptic fluid port 152 can serve as a chamber opening of the haptic fluid lumen 106. Fluid within the haptic fluid lumen 106 can flow out of the haptic fluid lumen 106 through the haptic fluid port 152 and into the optic fluid chamber 108 via the pair of fluid channels 110 when the haptic 104 is coupled to the optic portion 102. Similarly, fluid within the optic fluid chamber 108 can flow out of the optic fluid chamber 108 through the pair of fluid channels 110 and into the haptic fluid lumen 106 through the haptic fluid port 152. A pair of outer apertures 156 and inner aperture 146 can serve as ends of the fluid channels 110.

As shown in FIGS. 1A and 1E, each of the haptics 104 can couple to the optic portion 102 at a reinforced portion 112. For example, the first haptic 104A can couple or be attached to the optic portion 102 at a first reinforced portion 112A and the second haptic 104B can couple or be attached to the optic portion 102 at the second reinforced portion 112B.

More specifically, the proximal attachment end 114 can couple to the protruding outer surface 154 of the posterior element 132. The protruding outer surface 154 can also be referred to as a "landing" or "haptic attachment landing." The protruding outer surface 154 can extend out radially from an outer peripheral surface 122 of the optic portion 102. For example, the protruding outer surface 154 can extend out radially from an outer peripheral surface 122 of the posterior element 132 of the optic portion 102. The protruding outer surface 154 can extend out radially from the outer peripheral surface 122 between about 10 microns and 1.0 mm or between about 10 microns and 500 microns.

The proximal attachment end 114 can have a substantially flat surface to adhere or otherwise couple to a substantially flat surface of the protruding outer surface 154. When the proximal attachment end 114 is coupled to the protruding outer surface 154, the haptic fluid port 152 can surround the outer apertures 156 of the fluid channels 110. The haptics 104 can be coupled or adhered to the optic portion 102 via biocompatible adhesives 150. In some embodiments, the adhesives 150 can be the same adhesives used to couple or adhere the anterior element 130 to the posterior element 132.

In some embodiments, the composite material can comprise a composite base material, an energy absorbing constituent, and a plurality of expandable components or shrinkable components (e.g., shrinkable and/or burstable microspheres). As previously discussed, one or more portions of each of the haptics 104 can be made of the composite material.

The composite base material can be comprised of hydrophobic acrylic materials. For example, the composite base material can be comprised of phenylethyl acrylate (PEA), a phenylethyl methacrylate (PEMA), or a combination thereof.

In one example embodiment, the composite base material can comprise a methacrylate-functional or methacrylic-functional cross-linkable polymer and reactive acrylic monomer diluents including lauryl methacrylate (n-dodecyl methacrylate or SR313) and ADMA. By controlling the amount of lauryl methacrylate (SR313) to ADMA, the overall corresponding hardness (i.e., more ADMA) or softness (i.e., more SR313) of the cured composite material can be controlled. The methacrylate-functional or methacrylic-functional cross-linkable polymer can be made using the cross-linkable polymer precursor formulation.

The cross-linkable polymer precursor formulation can comprise the same copolymer blend used to make the optic portion and the haptics. The copolymer blend can comprise an alkyl acrylate or methacrylate (e.g., n-butyl acrylate), a fluoro-alkyl (meth)acrylate (e.g., trifluoroethyl methacrylate), and a phenyl-alkyl acrylate (e.g., phenylethyl acrylate). For example, the copolymer blend can comprise n-butyl acrylate in the amount of about 41% to about 45% (wt %), trifluoroethyl methacrylate in the amount of about 20% to about 24% (wt %), and phenylethyl acrylate in the amount of about 28% to about 32% (wt %). The cross-linkable polymer precursor formulation can comprise or be made in part of the copolymer blend, a hydroxyl-functional acrylic monomer (e.g., HEA), and a photoinitiator (e.g., Darocur 4265 or a 50/50 blend of diphenyl(2,4,6-trimethylbenzoyl)-phosphine oxide and 2-hydroxy2-methylpropiophenone).

The composite base material can comprise the methacrylate-functional or methacrylic-functional cross-linkable polymer (as discussed above) in the amount of about 50% to about 65% (e.g., about 55% to about 60%) (wt %), the reactive acrylic monomer diluent lauryl methacrylate (SR313) in the amount of about 32% to about 38% (e.g., about 32.70%) (wt %), the reactive acrylic monomer diluent adamantly methacrylate (ADMA) in the amount of about 5% to about 9% (e.g., about 7.30%) (wt %).

The composite material can be made in several operations. The first operation can comprise preparing an uncolored composite base material. The second operation can comprise mixing the composite base material with an energy absorbing constituent, expandable components or shrinkable/burstable elements, and initiators such as one or more photoinitiators, thermal initiators, or a combination thereof. The third operation can comprise placing the uncured composite material into a desired location within the haptics 104 (e.g., in proximity to the channel 148), and curing the composite material in place.

For example, the uncolored composite base material can be mixed with an energy absorbing constituent such as a dye (e.g., Disperse Red 1 dye) or pigment (graphitized carbon black). The energy absorbing constituent will be discussed in more detail below.

In some embodiments, the expandable components can make up about 5.0% to about 15.0% by weight of a final formulation of the composite material. More specifically, the expandable components can make up about 8.0% to about 12.0% (e.g., about 10.0%) by weight of a final formulation of the composite material. In these and other embodiments, the energy absorbing constituent can make up about 0.044% to about 0.44% (or about 0.55%) by weight of the final formulation of the composite material.

The photoinitiator can be Omnirad 2022 (bis(2,4,6-trimethylbenzoyl)phenyl-phosphineoxide/2-hydroxy-2-methyl-1-phenyl-propan-1-one). The photoinitiator can make up about 1.30% by weight of a final formulation of the composite material. In addition, the composite material can also comprise a thermal initiator. The thermal initiator can make up about 1.00% by weight of a final formulation of the composite material. In some embodiments, the thermal initiator can be a dialkyl peroxide such as Luperox® peroxide. In other embodiments, the thermal initiator can be Perkadox.

In some embodiments, the energy absorbing constituent can absorb the external energy (e.g., laser energy), convert the energy to heat, and conduct the energy to the composite base material to expand the composite base material.

In some embodiments, the expandable components can be expandable microspheres comprising an expandable thermoplastic shell and a blowing agent contained within the expandable thermoplastic shell. The microspheres can be configured to expand such that a diameter of at least one of the microspheres can increase about 2× the original diameter. In other embodiments, the microspheres can be configured to expand such that the diameter of at least one of the microspheres can increase about 4× or four times the original diameter. further embodiments, the microspheres can be configured to expand such that the diameter of at least one of the microspheres can increase between about 2× and about 4× (or about 3.5×) the original diameter. For example, the microspheres can have a diameter of about 12 μm at the outset. In response to an external energy applied or directed at the composite material or in response to energy transferred or transmitted to the microspheres, the diameter of the microspheres can increase to about 40 μm.

The volume of at least one of the microspheres can be configured to expand between about ten times (10×) to about 50 times (50×) in response to the external energy applied or directed at the composite material or in response to energy transferred or transmitted to the microspheres.

In some embodiments, the blowing agent can be an expandable fluid, such as an expandable gas. More specifically, the blowing agent can be a branched-chain hydrocarbon. For example, the blowing agent can be isopentane. In other embodiments, the blowing agent can be or comprise cyclopentane, pentane, or a mixture of cyclopentane, pentane, and isopentane.

Each of the expandable components can comprise a thermoplastic shell. A thickness of the thermoplastic shell can change as the expandable component increases in size. More specifically, the thickness of the thermoplastic shell can decrease as the expandable component increases in size. For example, when the expandable components are expandable microspheres, the thickness of the thermoplastic shell (i.e., its thickness in a radial direction) can decrease as the diameter of the expandable microsphere increases.

In some embodiments, the thermoplastic shell can be made in part of nitriles or acrylonitrile copolymers. For example, the thermoplastic shell can be made in part of acrylonitrile, styrene, butadiene, methyl acrylate, or a combination thereof.

As previously discussed, the expandable components can make up between about 8.0% to about 12% by weight of a final formulation of the composite material. The expandable components can make up about 10% by weight of a final formulation of the composite material.

The expandable components can be dispersed or otherwise distributed within the composite base material making up the bulk of the composite material. The composite base material can serve as a matrix for holding or carrying the expandable components. The composite material can expand in response to an expansion of the expandable components (e.g., the thermoplastic microspheres). For example, a volume of the composite material can increase in response to the expansion of the expandable components.

The composite material also comprises an energy absorbing constituent. In some embodiments, the energy absorbing constituent can be an energy absorbing colorant.

In certain embodiments, the energy absorbing colorant can be an energy absorbing dye. For example, the energy absorbing dye can be an azo dye. In some embodiments, the azo dye can be a red azo dye such as Disperse Red 1 dye. In other embodiments, the azo dye can be an orange azo dye such as Disperse Orange dye (e.g., Disperse Orange 1), a yellow azo dye such as Disperse Yellow dye (e.g., Disperse Yellow 1), a blue azo dye such as Disperse Blue dye (e.g., Disperse Blue 1), or a combination thereof.

In additional embodiments, the energy absorbing colorant can be or comprise a pigment. For example, the energy absorbing colorant can be or comprise graphitized carbon black as the pigment.

Similar to the expandable components, the energy absorbing constituent can be dispersed or otherwise distributed within the composite base material making up the bulk of the composite material. The composite base material can serve as a matrix for holding or carrying the expandable components and the energy absorbing constituent.

As previously discussed, the energy absorbing constituent can make up between about 0.025% to about 1.0% (or, more specifically, about 0.045% to about 0.45%) by weight of a final formulation of the composite material.

The energy absorbing constituent (e.g., azo dye, graphitized carbon black, or a combination thereof) can absorb or capture an external energy (e.g., light energy or, more specifically, laser light) applied or directed at the composite material. The energy absorbing constituent can absorb or capture the external energy and then transform or transfer the energy into thermal energy or heat to the expandable components.

The thermoplastic shell can soften and begin to flow as thermal energy is transferred or transmitted to expandable components. The thermoplastic shell of the expandable components can then begin to thin or reduce in thickness in response to the thermal energy transferred or transmitted to the expandable components. As the thermoplastic shell begins to soften and reduce in thickness, the blowing agent within the expandable components can expand. The blowing agent can also expand in response the thermal energy or heat transferred or transmitted to the expandable components. Expansion of the blowing agents can cause the expandable components (e.g., the thermoplastic microspheres) to expand or increase in volume. This ultimately causes the composite material to expand or increase in volume.

As previously discussed, the external energy can be laser light 125 and the energy absorbing constituent can absorb or capture the laser light 125 directed at the composite material and transform or transfer the light energy into thermal energy or heat to the expandable components. The blowing agent within the expandable components can expand or become energized in response to the thermal energy or heat. The expandable components and, ultimately, the composite material can expand or increase in volume in response to this light energy directed at the composite material.

As previously discussed, in some embodiments, the composite material can comprise the composite base material, the energy absorbing constituent, and a plurality of shrinkable components (e.g., shrinkable and/or burstable microspheres). The shrinkable and/or burstable microspheres can be dispersed or otherwise distributed within the composite base material along with the energy absorbing constituent. The composite base material can serve as a matrix for holding or carrying the shrinkable and/or burstable microspheres and the energy absorbing constituent.

The shrinkable or burstable microspheres can comprise an inner phase and one or more vacuum voids contained within a thermoplastic shell. The shrinkable microspheres can be configured to shrink or contract in size such that a diameter of at least one of the microspheres can decrease by about one-half of the original diameter.

For example, the shrinkable microspheres can initially be made with a diameter of between about 50 μm and 100 μm. In response to an external energy applied or directed at the composite material or in response to energy transferred or transmitted to the shrinkable microspheres, the diameter of the shrinkable microspheres can decrease to between about 25 μm and 50 μm.

The inner phase can be a fluid capable of undergoing one or more phase changes. In some embodiments, the inner phase can be configured to undergo a phase change from a vapor into a liquid phase at a temperature below a boiling point of the inner phase. When the inner phase is encapsulated within the thermoplastic shell, the one or more vacuum voids can be formed when the inner phase condenses into the liquid phase within the thermoplastic shell.

In one embodiment, the inner phase can be or comprise water. In this embodiment, the vacuum voids can be formed when the water vapor within the thermoplastic shell condenses into liquid water.

In other embodiments, the inner phase can be or comprise ethylene glycol (which has a higher boiling point than water). In further embodiments, the inner phase can be or comprise a silicone-based fluid such as certain cyclic siloxanes (e.g., hexamethylcyclotrisiloxane). In additional embodiments, the inner phase can be or comprise polydimethylsiloxane (PDMS) oligomers or certain types of hydrofluoroethers.

The thermoplastic shell can begin to soften and flow as thermal energy is transferred or transmitted to the shrinkable microspheres from the energy absorbing constituent. When the external energy is laser light 125, the energy absorbing constituent can absorb or capture the laser light 125 directed at the composite material and transform the light energy into thermal energy or heat.

The thermoplastic shell of the shrinkable microspheres can be configured to soften or begin to flow at a temperature above a glass transition temperature ($Tg_{shell}$) of the thermoplastic shell. The thermoplastic shell can also begin to thin out at a temperature above a glass transition temperature of the thermoplastic shell. When the thermoplastic shell is softened or thinned, the thermoplastic shell can collapse and decrease in size due to the external pressure surrounding the thermoplastic shell as well as due to the vacuum within the thermoplastic shell.

In some embodiments, at least some of these microspheres can also be configured to burst as the thermoplastic shell disintegrates or ruptures in response to the external energy directed at the first composite material. In these embodiments, the inner phase of the burstable microspheres can be dissolved into the surrounding haptic material or silicone oil.

In some embodiments, the thermoplastic shell can be or is made in part of polyacrylonitrile. In some embodiments, the thermoplastic shell can be or is made in part of polystyrene. In further embodiments, the thermoplastic shell can be or is made in part of poly(methyl methacrylate). The thermoplastic shell can also comprise a photoinitiator (e.g., a UV initiator). For example, the photoinitiator can be Omnirad 2022 (bis(2,4,6-6 trimethylbenzoyl)phenyl-phosphineoxide/

2-hydroxy-2-methyl-1-phenyl-propan-1-one). The thermoplastic shell can be formed when monomers of the shell material, along with the photoinitiator, are curved via UV curing.

The thermoplastic shell can re-form in its hardened state or become glassy once again when the temperature is below a glass transition temperature of the thermoplastic shell (i.e., when the external energy is no longer directed at the composite material). The diameter of the shrinkable microspheres can be reduced when the thermoplastic shell re-forms around the inner phase in the liquid phase and the space formerly occupied by the one or more vacuum voids is displaced.

Figure 2:
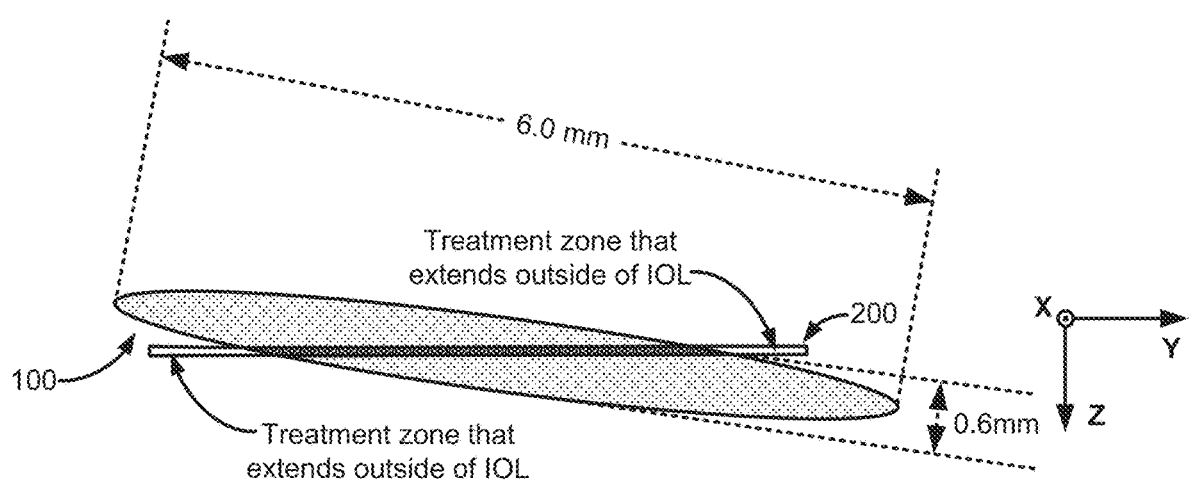
FIG. 2 is a schematic drawing showing a flattened ellipse representing a tilted IOL and a thin elongated rectangle representing a treatment zone of a laser that can be used to adjust the base power of the IOL.

FIG. 2 is a schematic drawing showing a flattened ellipse representing a part of a tilted IOL 100 and a thin elongated rectangle representing a treatment zone 200 of a laser that can be used to adjust the base power of the IOL 100. In some embodiments, the IOL 100 can be titled by a tilt angle of between 4.0 degrees and 8.0 degrees. For example, the IOL 100 can be tilted with respect to a line of sight of a subject when the IOL 100 is implanted within an eye of the subject.

As shown in FIG. 2, the tilt of the IOL 100 can make it challenging to post-operatively adjust a base power of the IOL 100 by directing laser light 125 (e.g., laser pulses) at the tilted IOL 100.

For example, an adjustment protocol or treatment protocol may require that a plurality of laser pulses be directed at multiple locations along one haptic 104A of the IOL 100 followed by additional laser pulses directed at multiple locations along another haptic 104B of the IOL 100 (see, e.g., FIG. 1A) in quick succession.

The adjustment protocol or treatment protocol can often require the subject to lie in a supine position. In this case, the optical axis of the laser can be vertical or in the Z-direction. The laser beam of the laser (e.g., a femtosecond laser) can be typically scanned with a pair of orthogonal galvanometric scanners in a horizontal X-Y plane. This scanning can be done on the order of a few milliseconds. However, the vertical position (or Z-position) of the treatment site is typically adjusted by a pair of adjustable nearly confocal lenses. The Z-positioning or scanning is slower than the X/Y scan and cannot keep up with the round trip scanning time of the X/Y scan. Thus, the optimal or preferred treatment zone of the laser is a substantially planar treatment zone 200 or a treatment zone 200 that is perpendicular (or substantially perpendicular) to the optical axis of the laser.

As shown in FIG. 2, when the IOL 100 is tilted, the substantially planar treatment zone 200 goes beyond the confines of the IOL 100. This means that when the IOL 100 is tilted, the laser may inadvertently damage the patient's eye via exposure to laser energy. Moreover, when the IOL 100 is tilted, the substantially planar treatment zone 200 means that the laser makes contact with the IOL 100 at different depths, which can cause any desired shape changes of the IOL 100 to be uneven. As such, there is a need to address the above-mentioned shortcomings caused by the tilt of the IOL 100 to correct for such tilt.

Figure 3:
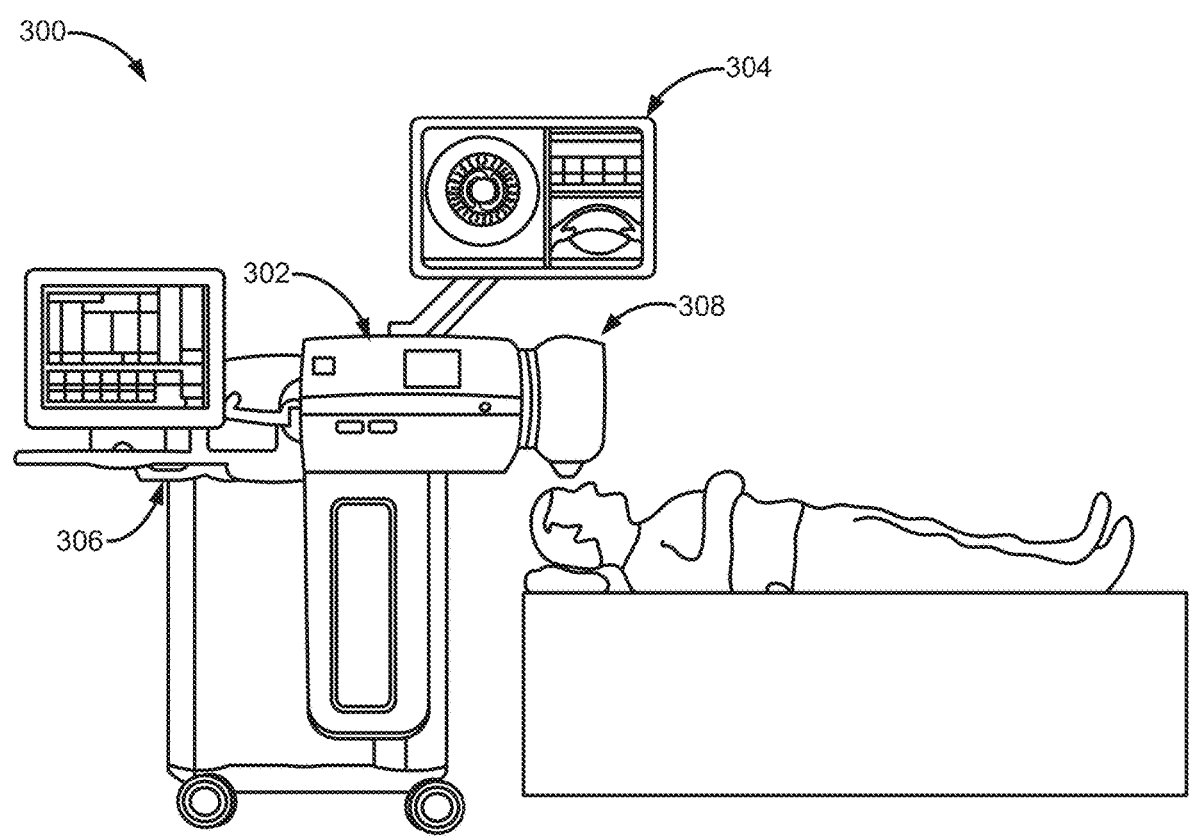
FIG. 3 illustrates an ophthalmic system configured to compensate for a tilt of the IOL or adjust the tilt of the IOL.

FIG. 3 illustrates an ophthalmic system 300 configured to compensate for a tilt of the IOL 100 and adjust the IOL 100 post-operatively. For example, the system 300 can be used to conduct an IOL adjustment procedure once the IOL 100 has been implanted within an eye of a subject. In some embodiments, the IOL adjustment procedure may require that a tilt of the implanted IOL be compensated for or corrected in order to place the IOL 100 in position for the remainder of the adjustment procedure.

The system 300 can comprise an optical coherence tomography (OCT) imaging apparatus 302 configured to produce one or more OCT images of an eye of a subject or patient having the IOL 100 implanted within the eye.

The system 300 can also comprise one or more electronic displays 304 and a control unit 306. The control unit 306 and the one or more electronic displays 304 can be communicatively coupled to one another and to the OCT imaging apparatus 302.

At least one of the electronic displays 304 can display the one or more OCT images captured by the OCT imaging apparatus 302. The OCT images can be displayed on the electronic display 304 in real-time while a user (e.g., a clinician, surgeon, or other ophthalmic professional) operates the system 300.

The OCT imaging apparatus 302 can generate an imaging beam that is used to scan the eye of the subject. The imaging beam can be directed into the eye by a beam splitter. Light scattered from ocular anatomical structures and implanted structures (e.g., the IOL 100) within the eye can be reflected back and used by the OCT imaging apparatus 302 to form a cross-sectional image of the eye and any implants therein. For example, the OCT imaging apparatus 302 can generate the cross-sectional OCT image by measuring the echo time delay and intensity of the back-scattered or back-reflected light. The OCT measurements of echo time delays are based on correlation techniques that compare the back-scattered or back-reflected light signal against reference light signals traveling a known path length.

The OCT imaging apparatus 302 can comprise an OCT light source that generates light in a low-power visible wavelength. In other embodiments, the OCT light source can generate light in the near-infrared (NIR) range (i.e., at a wavelength between about 900 nm to about 1,400 nm).

For example, the OCT light source of the OCT imaging apparatus 302 can be a superluminescent diode. The OCT imaging apparatus 302 can also comprise an interferometer such as a Michelson interferometer, a reference mirror, galvoscanners used to scan the imaging beam across the eye, and a spectrometer.

In some embodiments, the OCT imaging apparatus 302 can be communicatively coupled to the control unit 306 and one or more processors of the control unit 306 can be programmed to process imaging signals and control the various hardware components of the OCT imaging apparatus 302.

In one embodiment, the OCT imaging apparatus 302 can be a spectral-domain OCT (SD-OCT). In other embodiments, the OCT imaging apparatus 302 can be a swept-source OCT (SS-OCT), a frequency domain OCT, a Fourier domain OCT, or a complex Fourier OCT.

The OCT imaging apparatus 302 can also produce three-dimensional (3D) composite OCT images by combining two-dimensional (2D) cross-sectional OCT images.

Referring now also to FIGS. 4A-4C and FIGS. 5A-5B, the system 300 can comprise a fixation target source 400 configured to generate a moveable fixation target 404 (see FIGS. 4A-4C) that is visible to the eye of the subject. As will be discussed in more detail in the following sections, the fixation target 404 can be configured to be moved until a transverse plane 502 (see FIGS. 5A and 5B) of the IOL 100 is perpendicular or substantially perpendicular to an optical axis 506 (see FIGS. 5A and 5B) of the ophthalmic system 300. For example, the fixation target 404 can be moved until the transverse plane 502 of the IOL 100 as shown in the one or more OCT images displayed on the electronic display 304 is perpendicular or orthogonal (or substantially perpendicular or orthogonal) to the optical axis 506 displayed on the electronic display 304.

The system 300 can also comprise an ophthalmic laser 308 configured to generate and direct pulses of laser light at the IOL 100 to adjust a base power or dioptric power of the IOL 100. The control unit 306 can be configured to control the ophthalmic laser 308. In some embodiments, the laser 308 can be a femtosecond laser.

In some embodiments, the optical axis 506 of the system 300 can refer to an optical axis or Z-axis of a focusing lens or focusing objective of the laser 308. In certain embodiments, moving the fixation target 404 can further comprise moving the fixation target 404 to a position that is not axially aligned with the optical axis 506 of the laser.

As shown in FIG. 3, the subject or patient can be lying supine during the IOL adjustment procedure. In these embodiments, the optical axis 506 can be oriented vertically.

In some embodiments, the fixation target source 400 can be a fixation light source (e.g., a low-power laser or laser pointer). In these embodiments, the fixation target 404 can be a fixation light such as a beam of light having a wavelength in a visible spectrum (e.g., between about 350 nm and 750 nm).

In certain embodiments, the fixation target source 400 can be moved by a user or operator of the system 300. In other embodiments, the fixation target source 400 can be automatically moved by the ophthalmic system 300.

In some embodiments, the fixation target 404 can be moved in response to a user input applied by a user or operator of the system 300 (e.g., to an input device such as a mouse or keyboard or a button or touchpad on a component of the system 300). In other embodiments, the fixation target 404 can be automatically moved by the system 300.

In other embodiments, the fixation target source 400 can be a target display 408 visible to the subject or patient. In these embodiments, the fixation target 404 can be a computer-generated graphic 410 (see FIGS. 4B and 4C) generated on the target display 408.

In some embodiments, the OCT imaging apparatus 302 and the laser 308 can be integrated with the ophthalmic system 300.

As previously discussed, the OCT images captured by the OCT imaging apparatus 302 can be displayed on an electronic display 304 of the system 300. The OCT images can guide an operator/user of the system 300 (e.g., a clinician, surgeon, or other ophthalmic professional) as the operator/user undertakes an IOL adjustment procedure. The IOL adjustment procedure can require that the transverse plane 502 of the IOL 100 be perpendicular or orthogonal (or substantially perpendicular or orthogonal) to the optical axis 506 of the laser 308 of the system 300.

In some embodiments, the OCT images displayed on the electronic display 304 can allow the operator/user, in real-time, to determine whether the transverse plane 502 of the IOL 100 is perpendicular or orthogonal (or substantially perpendicular or orthogonal) to the optical axis 506 of the laser 308. In these embodiments, the optical axis 506 can be displayed on the electronic display 304 alongside a cross-sectional OCT image of the IOL 100 showing the transverse plane 502 of the IOL 100.

In some embodiments, the ophthalmic system 300 can comprise a laser module, a laser controller, a plurality of beam splitters, a focusing objective, and a patient interface. The laser module can generate and emit a beam of laser pulses to point(s) or focus spot(s) within the implanted IOL 100 as dictated by the laser controller. The laser controller can also adjust certain beam parameters of the laser beam and control where the beam is directed within the eye. The laser controller can perform these functions by sending one or more power control signals and scanning control signals to the laser module.

The beam of laser light 125 or laser beam generated by the laser 308 can be guided into the eye by one or more beam splitters. A focusing objective can focus the laser beam using one or more objective lenses while the patient interface can stabilize the eyeball of the patient during the laser treatment.

In some embodiments, the laser 308 can be an ultrafast pulsed diode-pumped solid-state femtosecond laser. The laser 308 can generate laser pulses with a duration of nanoseconds ($10^{-9}$ sec), picoseconds ($10^{-12}$ sec), or femtoseconds ($10^{-15}$ sec). The laser pulses can be generated at a pulse repetition rate of between 1 kHz to up to 500 kHz. More specifically, the laser pulses can be generated at a pulse repetition rate of between about 10 kHz to about 100 kHz. In other embodiments, the laser pulses can be generated at a pulse repetition rate of between 0.1 kHz to 1,000 kHz.

In some embodiments, the laser beam generated by the laser 308 can have a wavelength of between about 900 nm and 1100 nm (i.e., in the near-infrared (NIR) range). For example, the laser beam generated by the laser 308 can have a wavelength of about 1030 nm.

In alternative embodiments, the laser beam generated by the laser 308 can be a green laser light with a wavelength between about 480 nm and 650 nm (e.g., 532 nm). In these embodiments, the laser 308 can be a neodymium-doped yttrium aluminum garnet (Nd:YAG) laser.

Figure 4A:
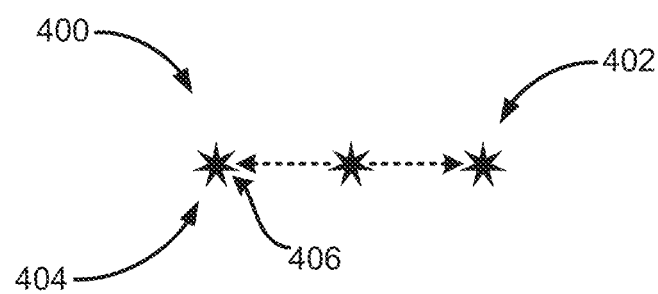
FIG. 4A illustrates one embodiment of a fixation target source implemented as a fixation light source.

FIG. 4A illustrates that the fixation target source 400 can be a fixation light source 402. In some embodiments, the fixation light source 402 can be a low-power laser or laser pointer. In these embodiments, the fixation target 404 can be a fixation light 406 such as a beam of visible light having a wavelength in a visible spectrum (e.g., between about 350 nm and 750 nm). The fixation light 406 can be visible to the subject or patient undergoing the IOL adjustment procedure.

In certain embodiments, the fixation light 406 can be moved in response to a user input applied by a user or operator of the ophthalmic system 300. For example, the fixation light 406 can be moved in response to a user input applied by the user or operator to an input device such as a mouse or keyboard communicatively coupled to the system 300 or a button or touchpad on a component of the system 300. In other embodiments, the fixation light 406 can be automatically moved by the system 300 based on calculations made by one or more processors of the control unit 306.

In some embodiments, the fixation light 406 can be moved by one or more beam splitters. In other embodiments, the fixation light 406 can be moved by physically moving the fixation light source 402.

Figure 4B:
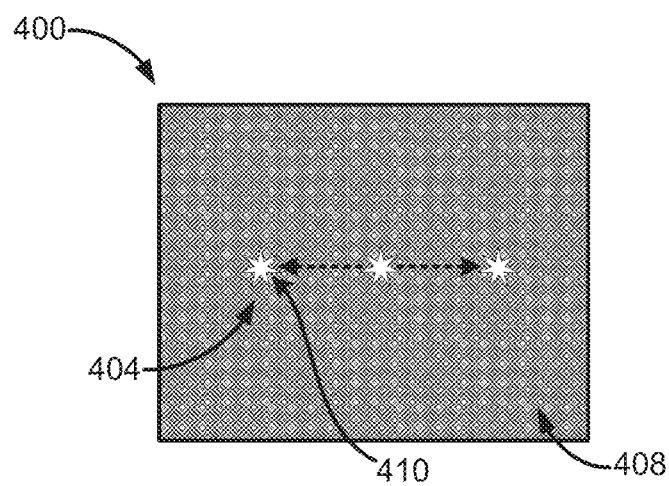
FIG. 4B illustrates another embodiment of a fixation target source implemented as a target display.

FIG. 4B illustrates that the fixation target source 400 can be a target display 408. The target display 408 can be positioned such that it is visible to the subject or patient during the IOL adjustment procedure. For example, the target display 408 can be positioned vertically above the subject when the subject is lying in the supine position.

In some embodiments, the target display 408 can be an electronic flat-panel display. For example, the target display 408 can be a liquid-crystal display (LCD) screen. In other embodiments, the target display 408 can be a light-emitting diode (LED) display, an organic light-emitting diode (OLED) display, or an active-matrix OLED (AMOLED)

display. In additional embodiments, the target display 408 can be projected onto a beam splitter that can be viewed by the subject or patient.

In these embodiments, the fixation target 404 can be a computer-generated graphic 410 generated on the target display 408. For example, the computer-generated graphic 410 can be a shining light graphic.

In some embodiments, the computer-generated graphic 410 serving as the fixation target 404 can be moved in response to a user input applied by a user or operator of the ophthalmic system 300. For example, the computer-generated graphic 410 can be moved in response to a user input applied by the user or operator to an input device such as a mouse or keyboard communicatively coupled to the system 300 or a button or touchpad on a component of the system 300. In other embodiments, the computer-generated graphic 410 can be automatically moved by the system 300 based on calculations made by one or more processors of the control unit 306.

Figure 4C:
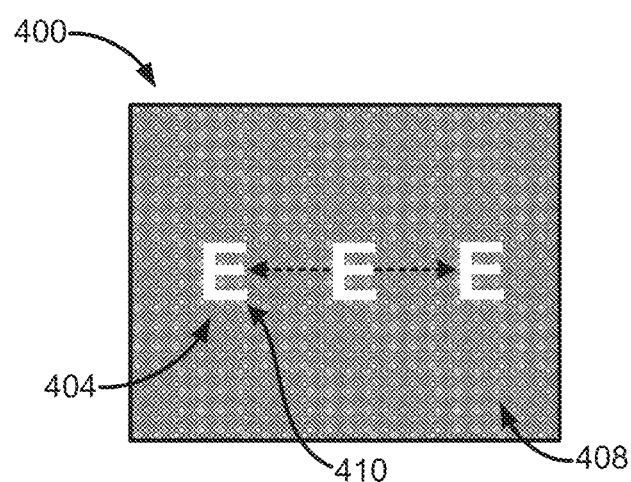
FIG. 4C illustrates another embodiment of a fixation target source implemented as a target display.

FIG. 4C illustrates that the computer-generated graphic 410 can also be in the form of a computer-generated letter, icon, or symbol. Moreover, the computer-generated graphic 410 can be a high-contrast letter, icon, or symbol.

Although FIGS. 4B and 4C illustrate the fixation target 404 as a light-colored graphic displayed on a dark-colored background. It is contemplated by this disclosure that the fixation target 404 can also be a dark-colored graphic displayed on a light-colored background.

Figure 5A:
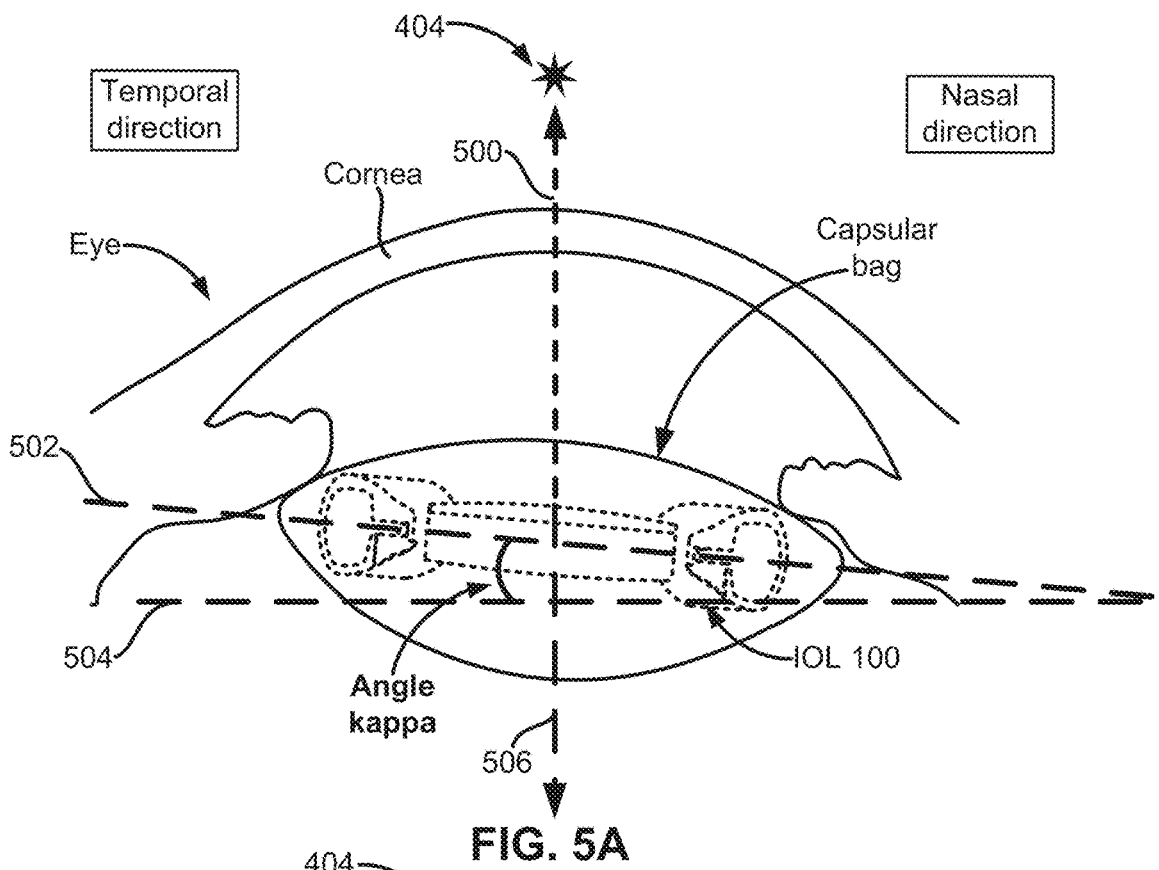
FIG. 5A is a schematic cross-sectional illustration of a tilted IOL that is implanted within an eye of the subject.

FIG. 5A is a schematic cross-sectional illustration of a tilted IOL 100 that is implanted within an eye of a subject. For example, the degree of tilt of the IOL 100 can be between about 4.0 degrees and about 8.0 degrees. More specifically, for example, the degree of tilt of the IOL 100 can be about 5.5 degrees.

Figure 7:
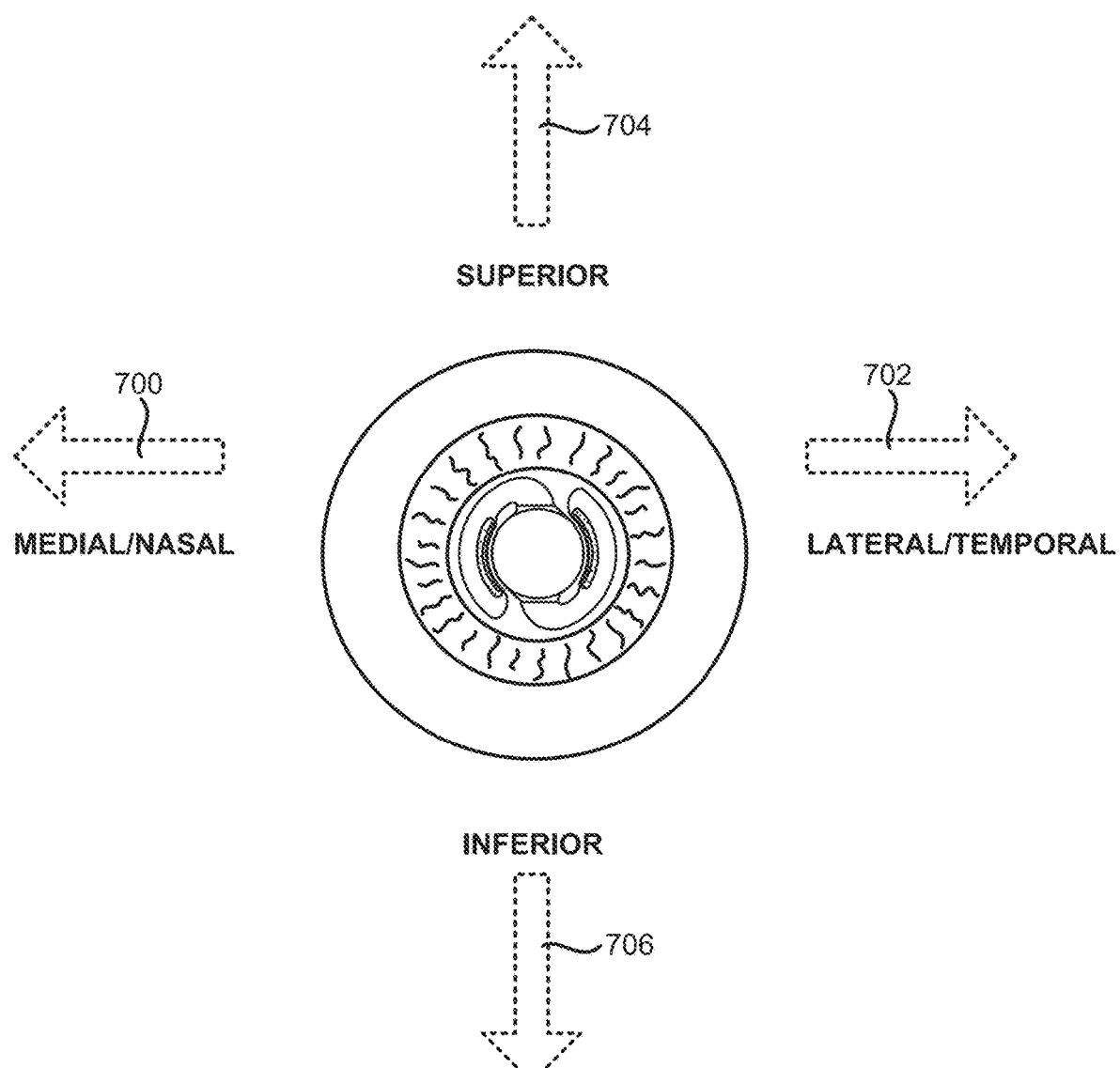
FIG. 7 illustrates several possible directions in which a fixation target can be moved.

In some embodiments, the tilt can be in the nasal direction (see, also, FIG. 7). The tilt can also be in the temporal direction, the superior direction, and/or the inferior direction (see, also, FIG. 7).

The implanted IOL 100 can also be tilted with respect to a line-of-sight 500 of the subject. For example, the IOL 100 can be tilted with respect to the line-of-sight 500 by an angle kappa (κ).

In some embodiments, the angle kappa can be an angle defined by the line-of-sight 500 and a pupillary axis. In other embodiments, the angle kappa can be defined by a transverse plane 502 of the implanted IOL 100 and a plane 504 that is perpendicular or orthogonal to (or substantially perpendicular or orthogonal to) an optical axis 506 of the ophthalmic system 300.

For example, the optical axis 506 can be the Z-axis of a focusing lens or focusing objective of the laser 308 of the ophthalmic system 300. The optical axis 506 can be oriented vertically or substantially vertically when the subject is lying in a supine position (see, for example, FIG. 3).

In some embodiments, the degree of tilt of the IOL 100 can be calculated or determined based on the OCT images captured by the OCT imaging apparatus 302 and displayed on the electronic display 304. In these embodiments, the plane 504 perpendicular or orthogonal to (or substantially perpendicular or orthogonal to) the optical axis 506 can be predetermined or determined based on the orientation of the laser 308 or the focusing lens or focusing objective of the laser 308. The transverse plane 502 of the implanted IOL 100 can be determined by a user or operator (e.g., a clinician, surgeon, or other ophthalmic professional) of the system 300 based on the OCT images captured by the OCT imaging apparatus 302 and displayed on the electronic display 304.

In other embodiments, the degree of tilt of the IOL 100 can be calculated or determined automatically by one or more processors of the control unit 306 of the system 300. For example, the one or more processors of the control unit 306 can analyze the OCT images captured by the OCT imaging apparatus 302 and determine or calculate the degree of tilt of the IOL 100 automatically without any or any substantial input from the user.

Figure 5B:
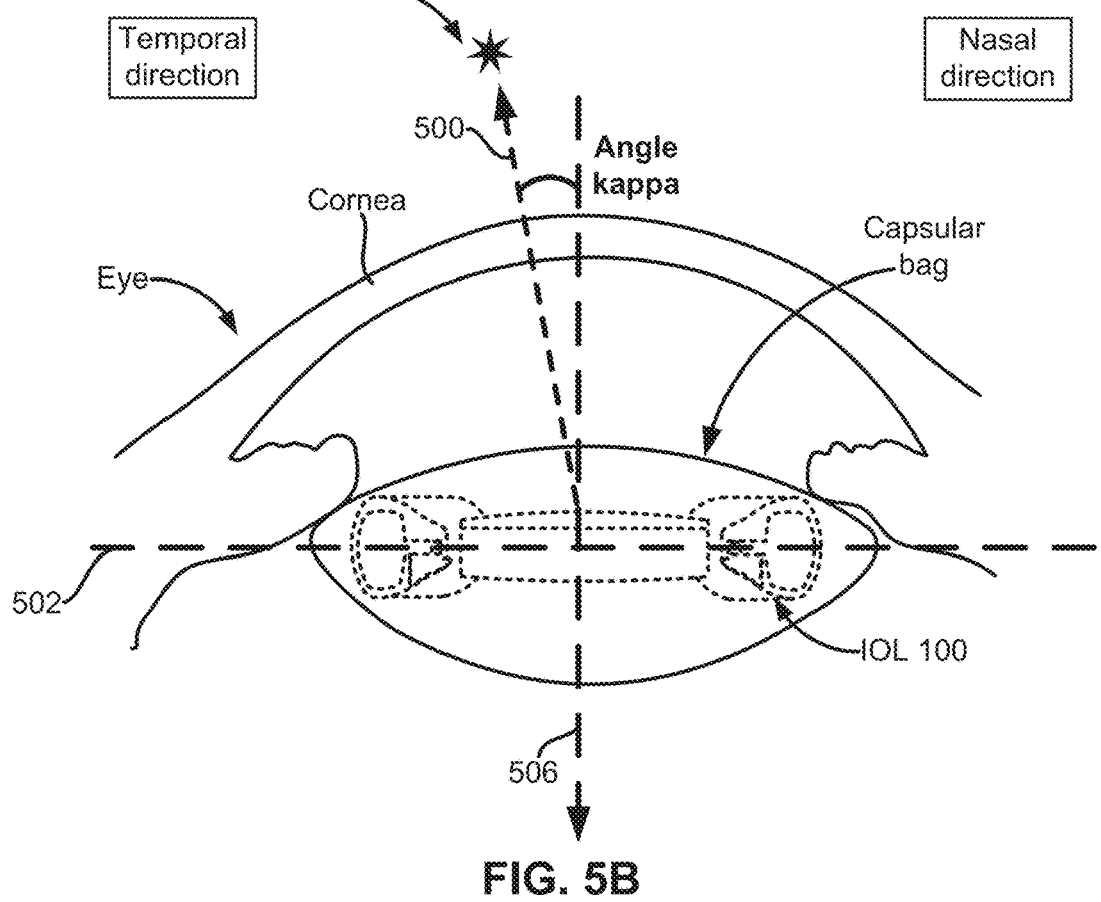
FIG. 5B is a schematic cross-sectional illustration showing a fixation target being used to correct for the tilt of the implanted IOL of FIG. 5A.

FIG. 5B is a schematic cross-sectional illustration showing a fixation target 404 being used to correct for the tilt of the implanted IOL 100. The subject can be instructed to focus on the fixation target 404 while the fixation target 404 is moved to a new location or position.

In other embodiments, the subject can be instructed to focus on the fixation target 404 after the fixation target 404 has been moved to a new location or position.

As shown in FIG. 5B, the fixation target 404 can be moved to a location or position not axially aligned with the optical axis 506 or Z-axis of the ophthalmic system 300 (if the subject is lying in the supine position).

The fixation target 404 can be moved in at least one of a medial/nasal direction, a lateral/temporal direction, an inferior direction, a superior direction, or a combination thereof, with respect to the subject.

The fixation target 404 can be moved until the transverse plane 502 of the implanted IOL 100 is perpendicular or substantially perpendicular to the optical axis 506 of the ophthalmic system 300 (e.g., the optical axis of the laser 308 of the ophthalmic system). In some embodiments, moving the fixation target 404 can comprise moving the fixation target 404 until the transverse plane 502 of the IOL, as shown in the OCT images displayed on the electronic display 304, is perpendicular or substantially perpendicular to the optical axis 506 of the ophthalmic system 300 displayed on the electronic display 304 (see also FIG. 6).

In some embodiments, the fixation target 404 can be moved based on the degree of tilt of the IOL 100. For example, the degree of tilt of the IOL 100 can be an angle kappa. In this example, the fixation target 404 can be moved until the angle formed by the new line-of-sight 500 and the optical axis 506 is equivalent or substantially equivalent to the angle kappa.

The fixation target 404 can be moved in response to a user input applied by a user or operator of the system 300 (e.g., to an input device such as a mouse or keyboard or a button or touchpad on a component of the system 300). In other embodiments, the fixation target 404 can be moved automatically by the control unit 306 of the system 300.

In some embodiments, the fixation target 404 can be maintained at this new location/position while laser light 125 (e.g., laser pulses) generated by the laser 308 is directed at the IOL 100. The laser light 125 can be used to adjust the base power of the IOL 100.

Figure 6:
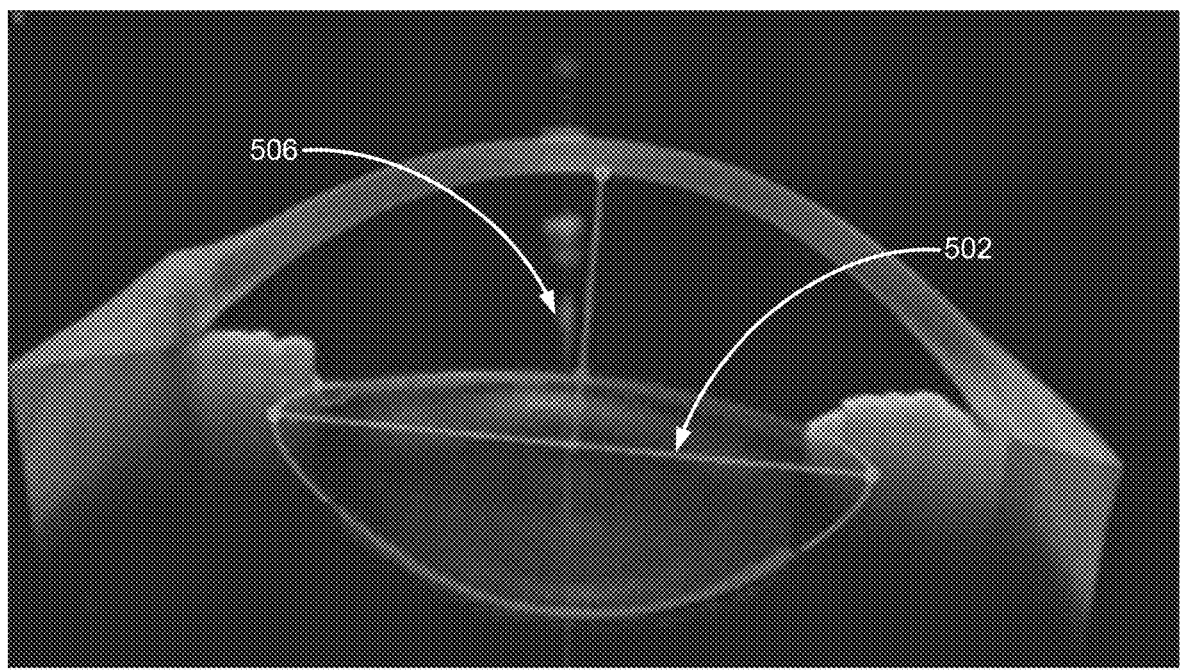
FIG. 6 is a cross-sectional OCT image showing a tilt of an implanted IOL.

FIG. 6 is a cross-sectional OCT image showing a tilt of the IOL 100 when the IOL 100 is implanted within an eye of the subject/patient. The cross-sectional OCT image can be displayed on an electronic display 304 of the system 300. As shown in FIG. 6, when the IOL 100 is tilted, the optical axis 506 of the ophthalmic system 300 is not perpendicular or orthogonal to a transverse plane 502 of the implanted IOL 100.

As previously discussed, due to certain limitations on the laser 308, the treatment zone or treatment region of the laser 308 may be substantially planar. Thus, one technical problem faced by the applicant is how to apply laser treatment to all necessary treatment sites on the tilted IOL 100 without putting the patient's eye at risk due to inadvertent exposure to laser energy. This risk is enhanced when such laser energy must be directed at one or more haptics 104 located peripheral to a central optic portion 102. Another technical problem faced by the applicant is that, when the IOL 100 is tilted, the substantially planar treatment zone 200 means that the laser makes contact with the IOL 100 at different depths, which can cause any desired shape changes of the IOL 100 to be uneven.

A technical solution discovered and developed by the applicant is the system and methods disclosed herein where a fixation target 404 (see FIGS. 4A-4C and 5A-5B) is used to adjust or correct for the tilt of the IOL 100. A fixation target 404 can be displayed or otherwise presented to the subject or patient and the subject or patient can track the fixation target 404 with the eye of the subject or patient without moving the head of the subject or patient. The fixation target 404 can be moved to a new location or position until the transverse plane 502 of the IOL 100 (e.g., as shown in a cross-sectional OCT image) is perpendicular or substantially perpendicular to the optical axis 506 of the laser 308 (thereby nullifying the angle kappa).

The fixation target 404 can be maintained at this new location/position while laser light 125 (e.g., laser pulses) generated by the laser 308 is directed at the IOL 100.

FIG. 7 illustrates several possible directions in which the fixation target 404 can be moved. As shown in FIG. 7, the fixation target 404 (any of the example fixation targets shown in FIGS. 4A-4C) can be moved in a medial direction 700, a lateral direction 702, a superior direction 704, an inferior direction 706, or any combination thereof.

With respect to the eyes of a subject/patient, the medial direction 700 can also be referred to as a nasal direction. Similarly, a lateral direction 702 can also be referred to as a temporal direction.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

It will be understood by one of ordinary skill in the art that the various methods disclosed herein may be embodied in a non-transitory readable medium, machine-readable medium, and/or a machine accessible medium comprising instructions compatible, readable, and/or executable by a processor or server processor of a machine, device, or computing device. The instructions can be stored in one or more computer-readable memory or storage devices that perform specified tasks when executed on a processor (e.g., CPU, GPU, or processor cores therein).

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A method of compensating for a tilt of an intraocular lens (IOL) with optical coherence tomography (OCT) guidance, comprising:
    capturing one or more OCT images of an eye of a subject using an OCT imaging apparatus, wherein the IOL is implanted within the eye of the subject;
    generating a fixation target such that the fixation target is visible to the eye of the subject; and
    moving the fixation target until a transverse plane of the IOL as shown in the one or more OCT images is perpendicular or substantially perpendicular to an optical axis of an ophthalmic system.

2. The method of claim 1, wherein the OCT imaging apparatus is communicatively coupled to an electronic display, and wherein moving the fixation target further comprises moving the fixation target until the transverse plane of the IOL as shown in the one or more OCT images displayed on the electronic display is perpendicular or substantially perpendicular to the optical axis displayed on the electronic display.

3. The method of claim 1, further comprising determining a degree of the tilt of the IOL and moving the fixation target based on the degree of tilt.

4. The method of claim 1, wherein the tilt of the IOL has a tilt angle between about 4.0 degrees and about 8.0 degrees.

5. The method of claim 1, wherein moving the fixation target further comprises moving the fixation target in at least one of a medial direction, a lateral direction, an inferior direction, and a superior direction with respect to the subject.

6. The method of claim 1, wherein the optical axis of the ophthalmic system is a Z-axis of a focusing lens or focusing objective of a laser of the ophthalmic system, and wherein moving the fixation target further comprises moving the fixation target to a position not axially aligned with the Z-axis.

7. The method of claim 6, wherein the optical axis is oriented vertically when the subject is lying in a supine position.

8. The method of claim 1, wherein the fixation target is a fixation light generated by a fixation light source.

9. The method of claim 8, wherein the fixation light is a beam of light having a wavelength in a visible spectrum.

10. The method of claim 8, wherein the fixation light is moveable in response to a user input by a user of the ophthalmic system.

11. The method of claim 8, wherein the fixation light source is configured to be automatically moved by the ophthalmic system.

12. The method of claim 1, wherein the fixation target is displayed on a target display visible to the subject.

13. The method of claim 12, wherein the fixation target is a computer-generated graphic.

14. The method of claim 1, wherein the OCT imaging apparatus is an integrated component of the ophthalmic system.

15. A method of adjusting an intraocular lens (IOL), comprising:
    capturing one or more OCT images of an eye of a subject using an OCT imaging apparatus, wherein the IOL is implanted within the eye of the subject;
    generating a fixation target such that the fixation target is visible to the eye of the subject;
    moving the fixation target until a transverse plane of the IOL as shown in the one or more OCT images is perpendicular or substantially perpendicular to an optical axis of an ophthalmic system; and
    directing a laser beam generated by a laser of the ophthalmic system at the IOL to adjust a base power of the IOL.

16. The method of claim 15, wherein the OCT imaging apparatus is communicatively coupled to an electronic display, and wherein moving the fixation target further comprises moving the fixation target until the transverse plane of the IOL as shown in the one or more OCT images displayed on the electronic display is perpendicular or substantially perpendicular to the optical axis displayed on the electronic display.

17. The method of claim 15, further comprising determining a degree of tilt of the IOL and moving the fixation target based on the degree of tilt.

18. The method of claim 17, wherein the degree of tilt of the IOL is between about 4.0 degrees and about 8.0 degrees.

19. The method of claim 15, wherein moving the fixation target further comprises moving the fixation target in at least one of a medial direction, a lateral direction, an inferior direction, and a superior direction with respect to the subject.

20. An ophthalmic system, comprising:
    an optical coherence tomography (OCT) imaging apparatus configured to produce one or more OCT images of an eye of a subject having an intraocular lens (IOL) implanted within the eye; and
    a fixation target source configured to generate a moveable fixation target that is visible to the eye of the subject, wherein the fixation target is configured to be moved until a transverse plane of the IOL as shown in the one or more OCT images is perpendicular or substantially perpendicular to an optical axis of the ophthalmic system.

* * * * *